(12) United States Patent
Kang et al.

(10) Patent No.: US 11,637,247 B2
(45) Date of Patent: Apr. 25, 2023

(54) COMPOUND FOR OPTOELECTRONIC DEVICE AND ORGANIC OPTOELECTRONIC DEVICE AND DISPLAY DEVICE

(71) Applicant: SAMSUNG SDI CO., LTD., Yongin-si (KR)

(72) Inventors: Dong Min Kang, Yongin-si (KR); Jun Seok Kim, Yongin-si (KR); Nanheon Lee, Yongin-si (KR); Byoungkwan Lee, Yongin-si (KR); Sangshin Lee, Yongin-si (KR); Dongyeong Kim, Yongin-si (KR); Min Seok Seo, Yongin-si (KR); Eun Sun Yu, Yongin-si (KR); Ho Kuk Jung, Yongin-si (KR)

(73) Assignee: Samsung SDI Co., Ltd., Yongin-si (KR)

( * ) Notice: Subject to any disclaimer, the term of this patent is extended or adjusted under 35 U.S.C. 154(b) by 564 days.

(21) Appl. No.: 16/693,959

(22) Filed: Nov. 25, 2019

(65) Prior Publication Data
US 2020/0168813 A1     May 28, 2020

(30) Foreign Application Priority Data
Nov. 28, 2018  (KR) .......................... 10-2018-0149835

(51) Int. Cl.
| | | |
|---|---|---|
| C07D 403/04 | (2006.01) | |
| C07D 403/10 | (2006.01) | |
| H01L 51/00 | (2006.01) | |

(52) U.S. Cl.
CPC ........ H01L 51/0072 (2013.01); C07D 403/04 (2013.01); C07D 403/10 (2013.01); H01L 51/0052 (2013.01); H01L 51/0067 (2013.01)

(58) Field of Classification Search
CPC ... C07D 403/04; C07D 403/10; C07D 251/24
See application file for complete search history.

(56) References Cited

U.S. PATENT DOCUMENTS

| 5,061,569 A | 10/1991 | Vanslyke et al. |
|---|---|---|
| 2004/0086745 A1 | 5/2004 | Iwakuma et al. |

(Continued)

FOREIGN PATENT DOCUMENTS

| CN | 102227485 A | 10/2011 |
|---|---|---|
| CN | 103459375 A | 12/2013 |

(Continued)

OTHER PUBLICATIONS

Computer-generated English-language translation of WO-2019212287-A1.*

(Continued)

Primary Examiner — Vu A Nguyen
(74) Attorney, Agent, or Firm — Lee IP Law, P.C.

(57) ABSTRACT

A compound for an organic optoelectronic device is represented by Chemical Formula 1,

[Chemical Formula 1]

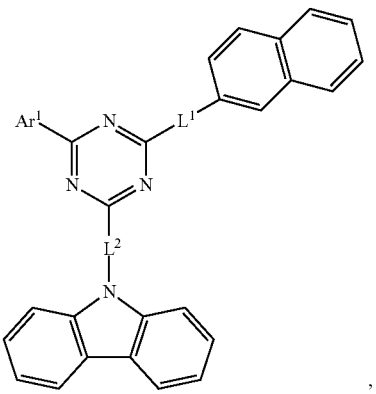

wherein $Ar^1$ may be a substituted or unsubstituted C6 to C18 aryl group, $L^1$ may be a substituted or unsubstituted C6 to C20 arylene group, a substituted or unsubstituted C2 to C20 heteroarylene group, or a combination thereof, and $L^2$ may be a single bond or a substituted or unsubstituted phenylene group.

12 Claims, 1 Drawing Sheet

(56) References Cited

U.S. PATENT DOCUMENTS

| | | |
|---|---|---|
| 2010/0127616 A1 | 5/2010 | Kai et al. |
| 2011/0240983 A1 | 10/2011 | Sekiguchi et al. |
| 2011/0248257 A1 | 10/2011 | Kim et al. |
| 2014/0008631 A1 | 1/2014 | Tsuji et al. |
| 2014/0034938 A1 | 2/2014 | Ishibashi et al. |
| 2014/0323723 A1 | 10/2014 | Ahn et al. |
| 2014/0361254 A1 | 12/2014 | Hwang et al. |
| 2016/0141503 A1 | 5/2016 | Yang |
| 2016/0218288 A1 | 7/2016 | Huh et al. |
| 2016/0225993 A1 | 8/2016 | Huh et al. |
| 2016/0276594 A1 | 9/2016 | Huh et al. |
| 2017/0005276 A1 | 1/2017 | Kim et al. |
| 2019/0214570 A1* | 7/2019 | Inayama .............. C07D 487/04 |
| 2020/0111967 A1* | 4/2020 | Lee ..................... H01L 51/0074 |

FOREIGN PATENT DOCUMENTS

| | | | | |
|---|---|---|---|---|
| CN | 103664894 A | * | 3/2014 | ........... C07D 401/14 |
| CN | 103664894 A | | 3/2014 | |
| CN | 111009612 A | | 4/2020 | |
| JP | 05-009471 A | | 1/1993 | |
| JP | 07-126615 A | | 5/1995 | |
| JP | 10-095973 A | | 4/1998 | |
| JP | 2010-138121 A | | 6/2010 | |
| JP | 2013-69703 | | 4/2013 | |
| JP | 2014-96417 | | 5/2014 | |
| JP | 2019-119723 A | | 7/2019 | |
| KR | 10-2012-0116282 A | | 10/2012 | |
| KR | 10-2014-0143042 A | | 12/2014 | |
| KR | 10-2015-0108332 | | 9/2015 | |
| KR | 10-2016-0029721 | | 3/2016 | |
| KR | 10-2016-0031425 | | 3/2016 | |
| KR | 10-2016-0031426 | | 3/2016 | |
| KR | 10-2016-0039535 | | 4/2016 | |
| KR | 10-2017-0134264 | | 12/2017 | |
| KR | 10-1832084 | | 2/2018 | |
| KR | 10-2018-0063708 | | 6/2018 | |
| KR | 10-2019-0086347 A | | 7/2019 | |
| KR | 10-2020-0006020 A | | 1/2020 | |
| TW | 201329201 A1 | | 7/2013 | |
| WO | WO 9509147 A1 | | 4/1995 | |
| WO | WO 03/080760 A1 | | 10/2003 | |
| WO | WO 2012/137958 A1 | | 10/2012 | |
| WO | WO 2013/073874 A1 | | 5/2013 | |
| WO | WO 2013-175747 A1 | | 11/2013 | |
| WO | WO 2014/054912 A1 | | 4/2014 | |
| WO | WO 2014-122933 A1 | | 8/2014 | |
| WO | WO 2016/052819 A1 | | 4/2016 | |
| WO | WO 2016/080749 A1 | | 5/2016 | |
| WO | WO-2019212287 A1 | * | 11/2019 | .............. B60L 15/08 |
| WO | WO 2020-101397 A1 | | 5/2020 | |

OTHER PUBLICATIONS

Computer-generated English-language translation of CN-103664894-A.*
Taiwanese Office action and Search Report dated Feb. 19, 2021.
Japanese Office Action dated Nov. 24, 2020.
Extended European Search Report dated Mar. 17, 2020.
Chinese Office Action dated Jun. 30, 2022, including Search Report dated Jun. 12, 2022.
Korean Notice of Allowance dated Aug. 16, 2022.
Korean Office action dated Dec. 21, 2021.
Decision on Patent Opposition dated Feb. 16, 2022.

* cited by examiner

COMPOUND FOR OPTOELECTRONIC DEVICE AND ORGANIC OPTOELECTRONIC DEVICE AND DISPLAY DEVICE

CROSS-REFERENCE TO RELATED APPLICATION

Korean Patent Application No. 10-2018-0149835, filed on Nov. 28, 2018, in the Korean Intellectual Property Office, and entitled: "Compound for Optoelectronic Device and Organic Optoelectronic Device and Display Device," is incorporated by reference herein in its entirety.

BACKGROUND

1. Field

Embodiments relate to a compound for an organic optoelectronic device, an organic optoelectronic device, and a display device.

2. Description of the Related Art

An organic optoelectronic device (such as an organic optoelectronic diode) is a device that converts electrical energy into photoenergy, and vice versa.

An organic optoelectronic device may be classified as follows in accordance with its driving principles. One is a photoelectric device where excitons generated by photoenergy are separated into electrons and holes and the electrons and holes are transferred to different electrodes respectively and electrical energy is generated, and the other is a light emitting device to generate photoenergy from electrical energy by supplying a voltage or a current to electrodes.

Examples of the organic optoelectronic device include an organic photoelectric device, an organic light emitting diode, an organic solar cell, and an organic photo conductor drum. Among them, the organic light emitting diode (OLED) has recently drawn attention due to an increase in demand for flat panel displays.

SUMMARY

Embodiments are directed to a compound for an organic optoelectronic device represented by Chemical Formula 1,

[Chemical Formula 1]

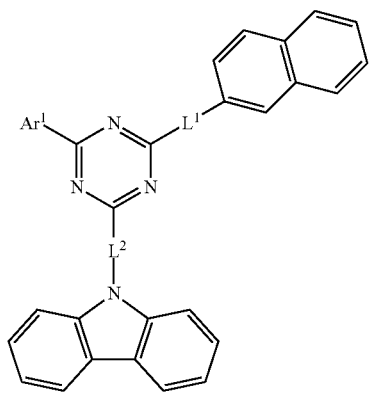

In Chemical Formula 1, $Ar^1$ may be a substituted or unsubstituted C6 to C18 aryl group, $L^1$ may be a substituted or unsubstituted C6 to C20 arylene group, a substituted or unsubstituted C2 to C20 heteroarylene group, or a combination thereof, and $L^2$ may be a single bond or a substituted or unsubstituted phenylene group.

Embodiments are also directed to a compound for an organic optoelectronic device, the compound having a structure in which an aryl group, a naphthyl group, and a carbazolyl group are each bonded to a same triazine group. The aryl group may be bonded to the triazine group via a single bond. The aryl group may be a substituted or unsubstituted C6 to C18 aryl group. The naphthyl group may be bonded to the triazine group via a first linking group that is bonded to the naphthyl group at position 2 or 3 of the naphthyl group. The first linking group may be a substituted or unsubstituted C6 to C20 arylene group, a substituted or unsubstituted C2 to C20 heteroarylene group, or a combination thereof. The carbazolyl group may be bonded to the triazine group via a second linking group that is bonded to the carbazolyl group at position 9 of the carbazolyl group. The second linking group may be a single bond or a substituted or unsubstituted phenylene group.

Embodiments are also directed to an organic optoelectronic device, including an anode and a cathode facing each other, and at least one organic layer disposed between the anode and the cathode. The organic layer may include a compound for an organic optoelectronic device according to an embodiment.

Embodiments are also directed to a display device. The display device may include an organic optoelectronic device according to an embodiment.

BRIEF DESCRIPTION OF THE DRAWINGS

Features will become apparent to those of skill in the art by describing in detail example embodiments with reference to the attached drawings in which.

DETAILED DESCRIPTION

Figure 1:
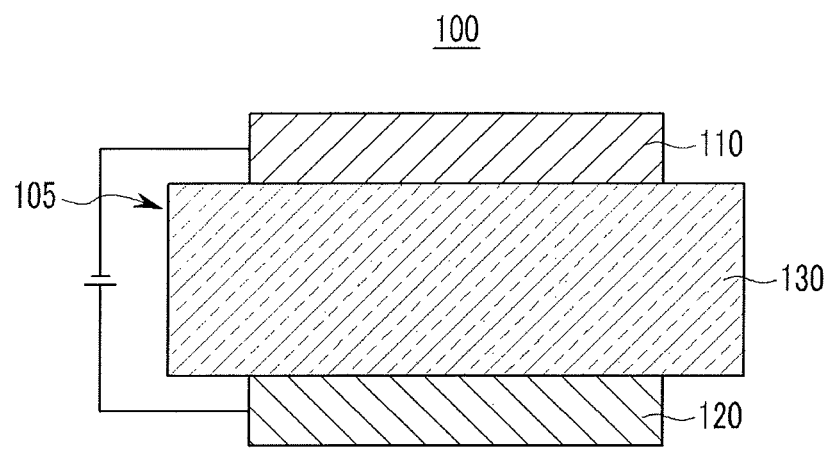
FIGS. 1 and 2 illustrate cross-sectional views showing organic light emitting diodes according to example embodiments.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey example implementations to those skilled in the art. In the drawing figures, the dimensions of layers and regions may be exaggerated for clarity of illustration. Like reference numerals refer to like elements throughout.

As used herein, when a definition is not otherwise provided, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 trifluoroalkyl group, a cyano group, or a combination thereof.

In one example, "substituted" refers to replacement of at least one hydrogen of a substituent or a compound by deuterium, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, or a C2 to C30 heteroaryl group. In addition, in specific examples, "substituted" refers to replacement of at least one hydrogen of a substituent or a compound by deuterium, a C1 to C20 alkyl group, a C6 to C30 aryl group, or a C2 to C30 heteroaryl group. In addition, in specific examples, "substituted" refers to replacement of at least one hydrogen of a substituent or a compound by deuterium, a C1 to C5 alkyl group, a C6 to C18 aryl group, a pyridinyl group, a quinolinyl group, an isoquinolinyl group, a dibenzofuranyl group, a dibenzothiophenyl group, or a carbazolyl group. In addition, in specific examples, "substituted" refers to replacement of at least one hydrogen of a substituent or a compound by deuterium, a C1 to C5 alkyl group, a C6 to C18 aryl group, a dibenzofuranyl group, or a dibenzothiophenyl group. In addition, in specific examples, "substituted" refers to replacement of at least one hydrogen of a substituent or a compound by deuterium, a methyl group, an ethyl group, a propyl group, a butyl group, a phenyl group, a biphenyl group, a terphenyl group, a naphthyl group, a triphenylenyl group, a dibenzofuranyl group, or a dibenzothiophenyl group.

As used herein, when a definition is not otherwise provided, "hetero" refers to one including one to three heteroatoms selected from N, O, S, P, and Si, and remaining carbons in one functional group.

In the present specification, "aryl group" refers to a group including at least one aromatic hydrocarbon c moiety, and may include a group in which all elements of the aromatic hydrocarbon moiety have p-orbitals which form conjugation, for example a phenyl group, a naphthyl group, and the like, a group in which two or more aromatic hydrocarbon moieties may be linked by a sigma bond, for example a biphenyl group, a terphenyl group, a quarterphenyl group, and the like, and a group in which two or more aromatic hydrocarbon moieties are fused directly or indirectly to provide a non-aromatic fused ring, for example a fluorenyl group, and the like.

The aryl group may include a monocyclic, polycyclic or fused ring polycyclic (i.e., rings sharing adjacent pairs of carbon atoms) functional group.

In the present specification, "heterocyclic group" is a generic concept of a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, "heteroaryl group" may refer to an aryl group including at least one heteroatom selected from N, O, S, P, and Si. Two or more heteroaryl groups may be linked by a sigma bond directly, or when the heteroaryl group includes two or more rings, the two or more rings may be fused. When the heteroaryl group is a fused ring, each ring may include one to three heteroatoms.

More specifically, the substituted or unsubstituted C6 to C30 aryl group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted triphenylene group, a substituted or unsubstituted perylenyl group, a substituted or unsubstituted fluorenyl group, a substituted or unsubstituted indenyl group, or a combination thereof, etc.

More specifically, the substituted or unsubstituted C2 to C30 heterocyclic group may be a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzothiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted dibenzofuranyl group, a substituted or unsubstituted dibenzothiophenyl group, or a combination thereof, etc.

In the present specification, hole characteristics refer to an ability to donate an electron to form a hole when an electric field is applied and that a hole formed in the anode may be easily injected into the light emitting layer and transported in the light emitting layer due to conductive characteristics according to a highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to a lowest unoccupied molecular orbital (LUMO) level.

A compound for an organic optoelectronic device according to an example embodiment is represented by Chemical Formula 1.

[Chemical Formula 1]

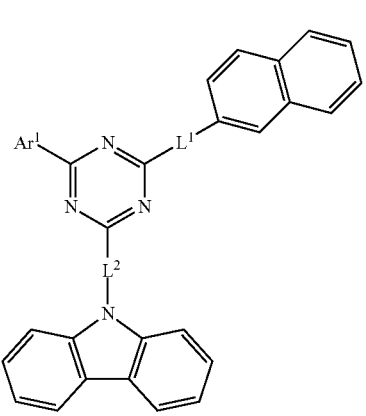

In Chemical Formula 1, $Ar^1$ may be a substituted or unsubstituted C6 to C18 aryl group, $L^1$ may be a substituted or unsubstituted C6 to C20 arylene group, a substituted or unsubstituted C2 to C20 heteroarylene group, or a combination thereof, and $L^2$ may be a single bond or a substituted or unsubstituted phenylene group.

The compound represented by Chemical Formula 1 has a structure in which an aryl group, a naphthyl group, and a 9-carbazolyl group are included around a triazine core simultaneously.

The naphthyl group may be linked to triazine at position 2 or 3 via a linking group.

The glass transition temperature of the compound may be improved by the 9-carbazole bonded to the triazine core, and the compound may have LUMO and T1 energies suitable for a red host from the naphthyl group substituted through the linking group. Thus, a red host exhibiting high efficiency/long life-span/low voltage driving characteristics may be provided.

According to the present example embodiment, the naphthyl group is substituted at a 2 or 3 position. Thus, a glass transition temperature may be increased compared with a case in which the naphthyl group is substituted at a 1 or 4 position. Thus, a compound according to the present example embodiment may provide increased thermal stability and improved life-span.

According to the present example embodiment, in Chemical Formula 1, $L^1$ may be a substituted or unsubstituted C6 to C20 arylene group, for example a substituted or unsubstituted phenylene group, or a substituted or unsubstituted biphenylene group.

For example, $L^1$ may be one of linking groups of Group I.

[Group I]

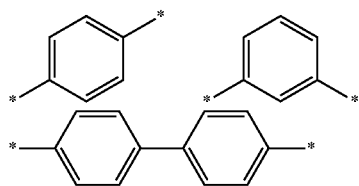

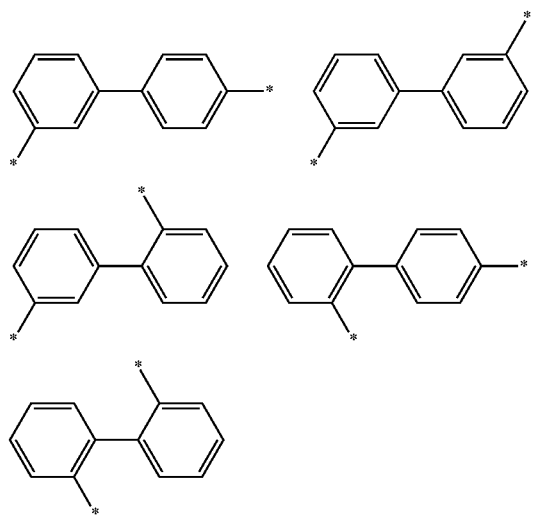

For example, $L^1$ may be a phenylene group.

According to the present example embodiment, in Chemical Formula 1, $Ar^1$ may be a substituted or unsubstituted phenyl group, a substituted or unsubstituted biphenyl group, or a substituted or unsubstituted terphenyl group.

For example, $Ar^1$ may be one of substituents of Group II.

[Group II]

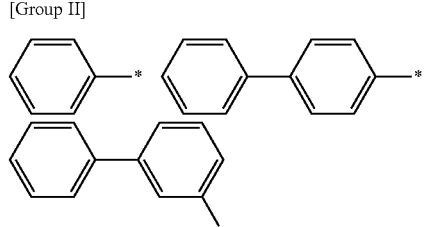

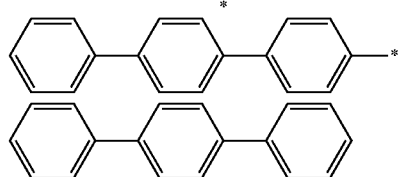

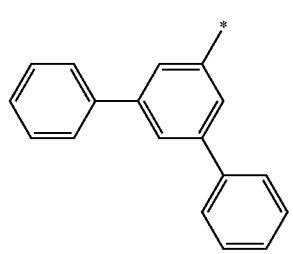

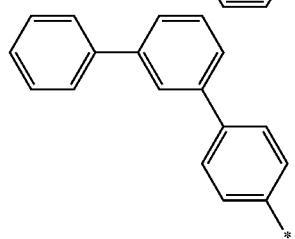

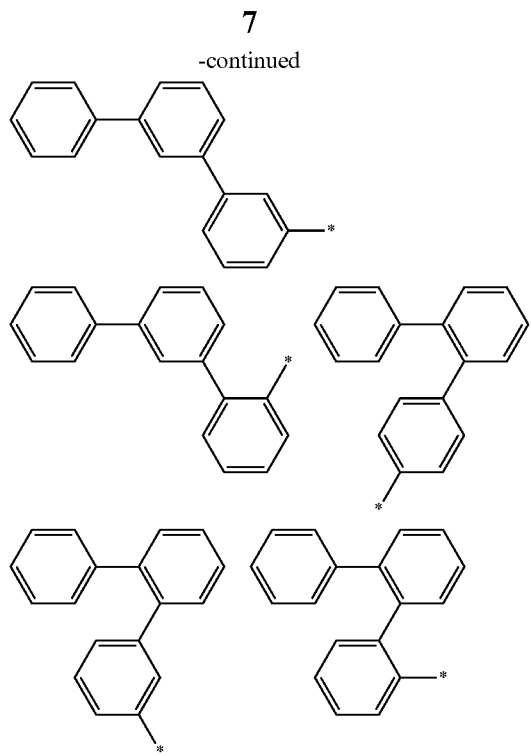
For example, $Ar^1$ may be a substituted or unsubstituted phenyl group or a substituted or unsubstituted biphenyl group.
In an example embodiment, the compound for the organic optoelectronic device may be one of compounds of Group A.
[Group A]
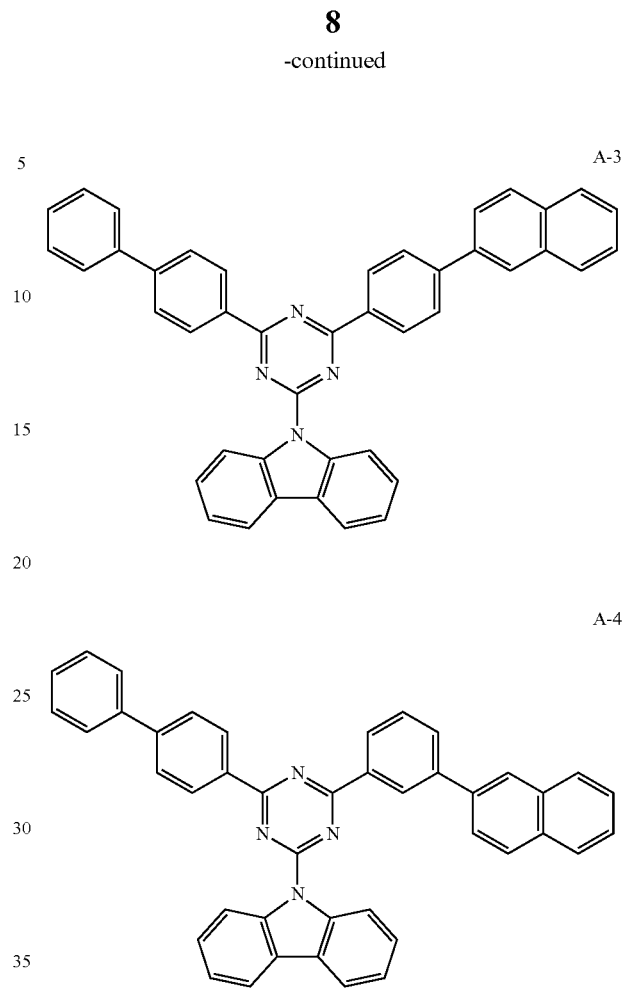
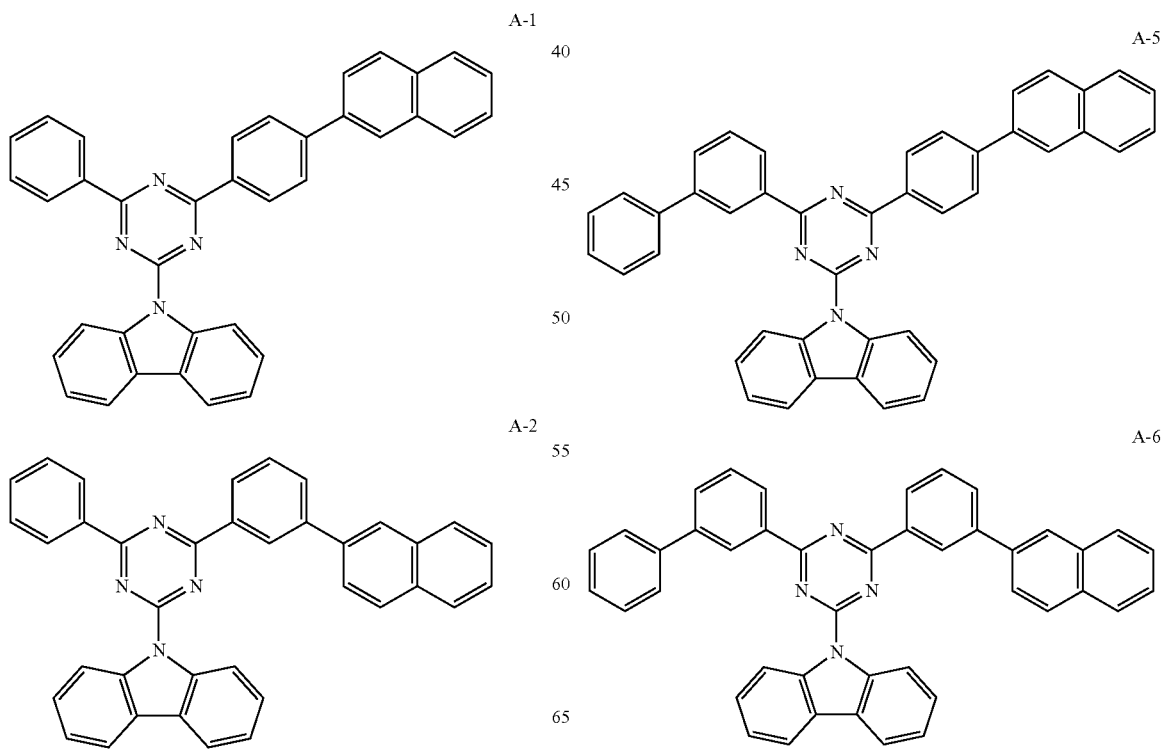

-continued
A-7
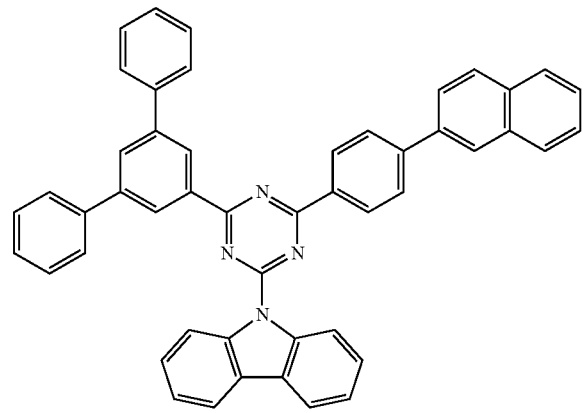
A-8
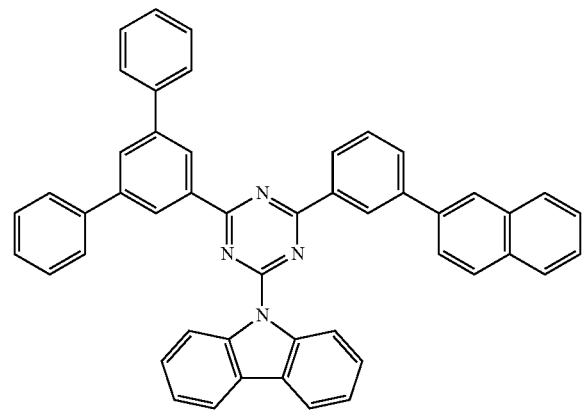
A-9
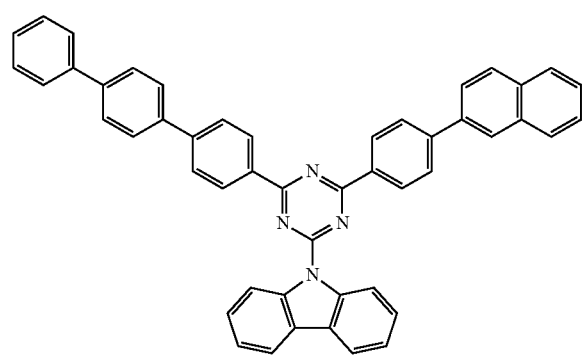
A-10
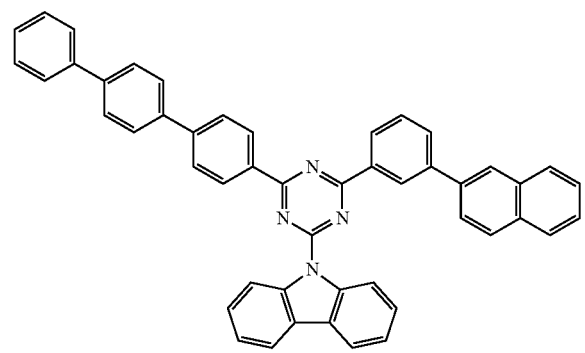
-continued
A-11
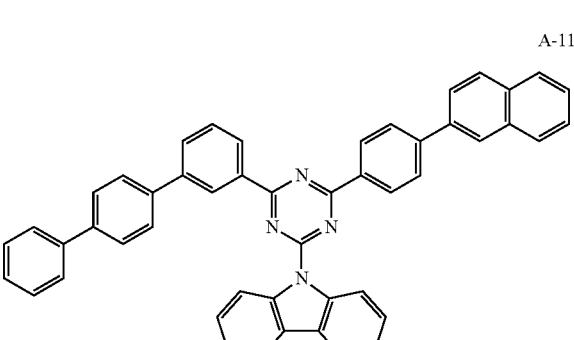
A-12
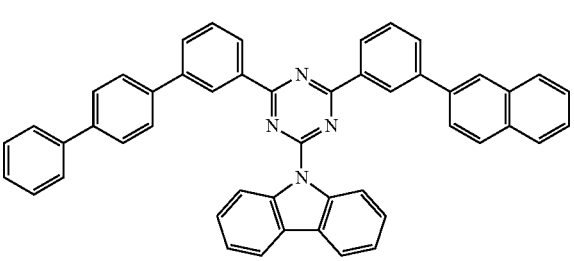
A-13
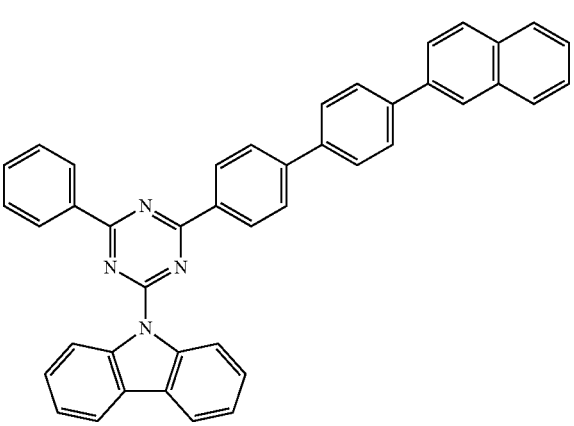
A-14
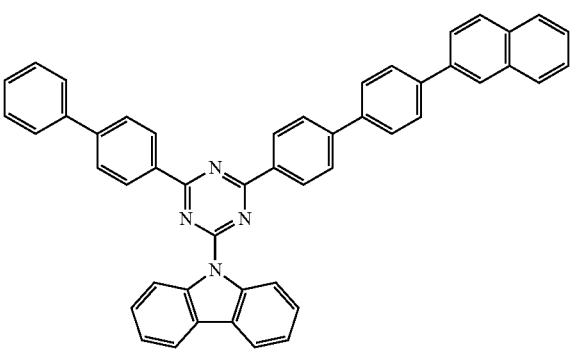

A-15
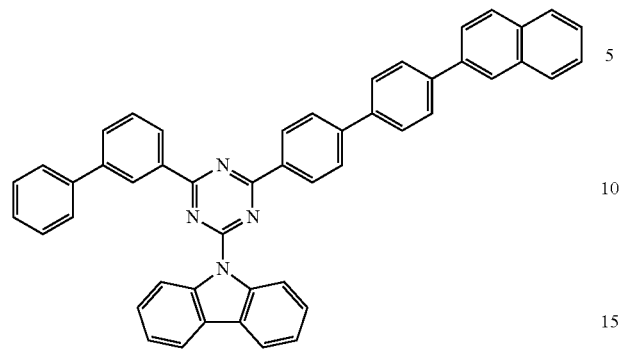
A-16
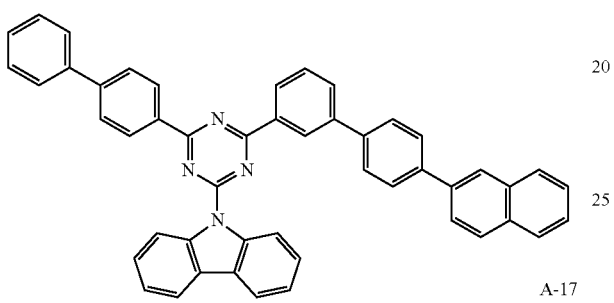
A-17
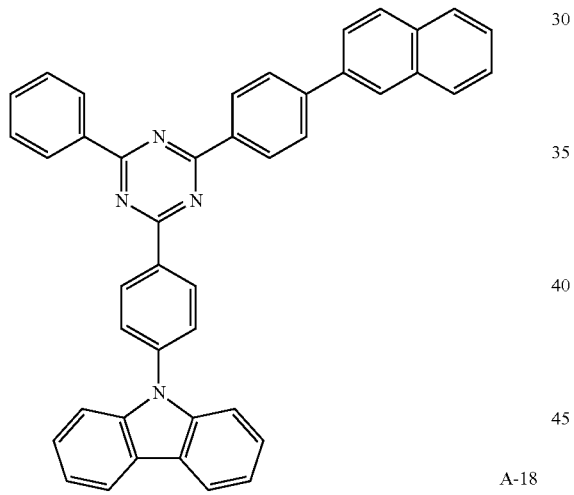
A-18
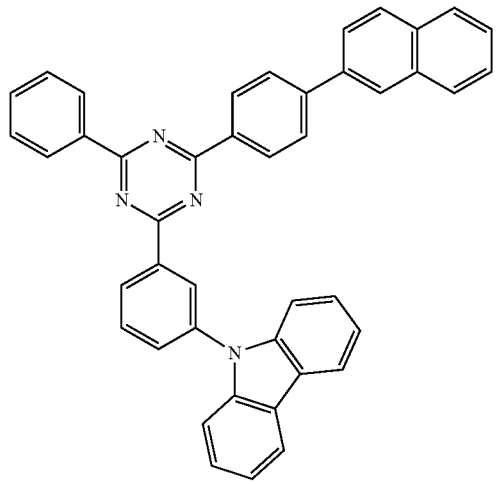
A-19
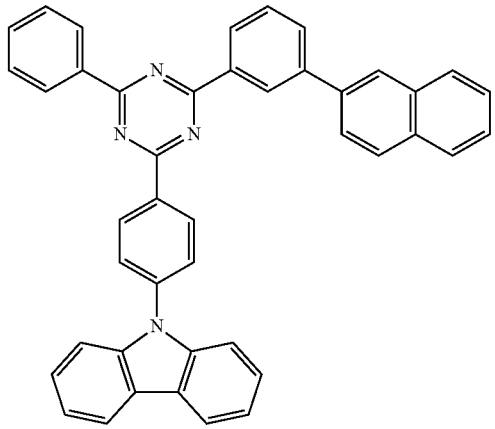
A-20
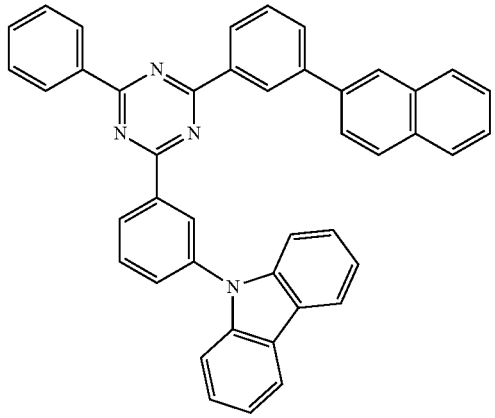
A-21
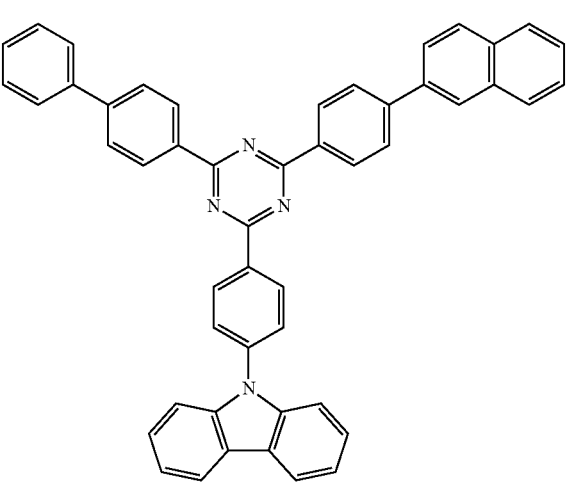

A-22
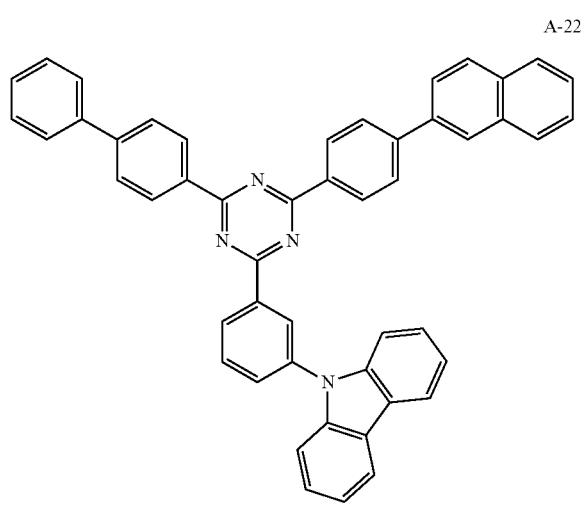
A-23
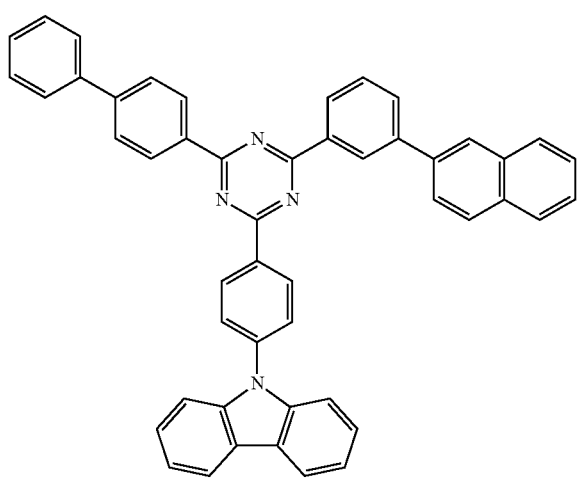
A-24
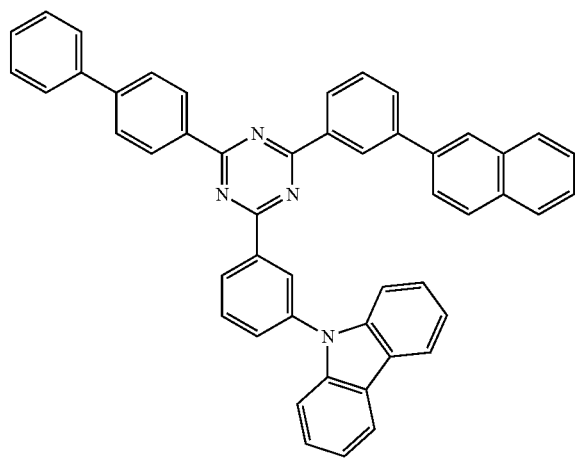
A-25
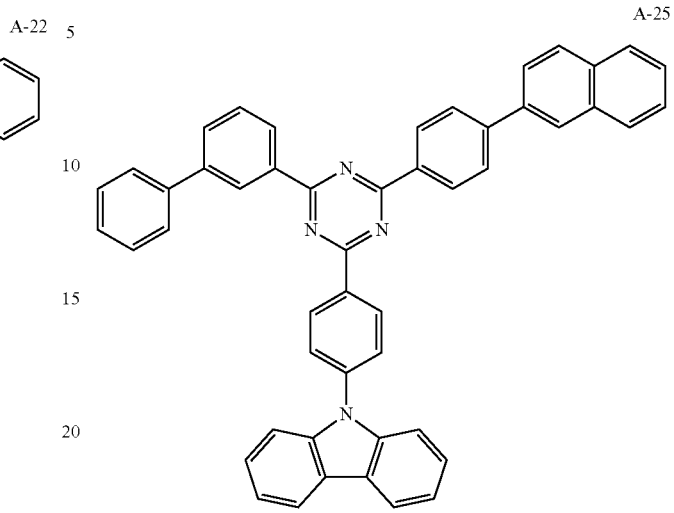
A-26
A-27
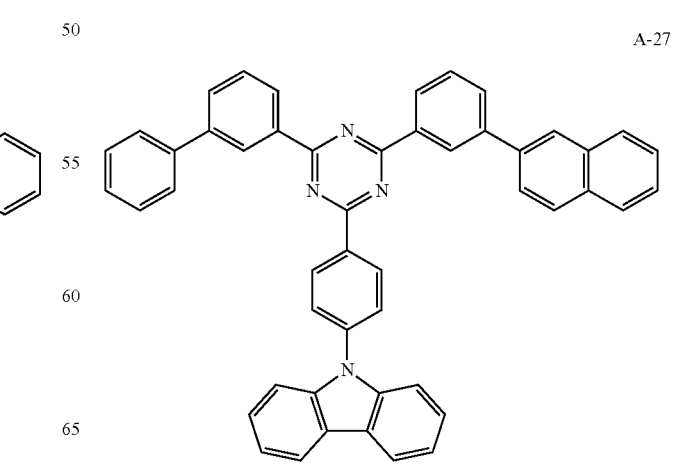

-continued

A-28

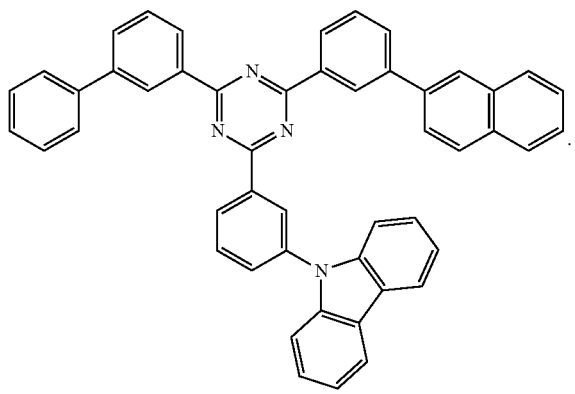

According to an example embodiment, an organic optoelectronic device includes a compound according to an embodiment.

The organic optoelectronic device may be a device that converts electrical energy into photoenergy and/or vice versa. The organic optoelectronic device may be, for example an organic photoelectric device, an organic light emitting diode, an organic solar cell, or an organic photoconductor drum.

Hereinafter, an organic light emitting diode, as one example of an organic optoelectronic device, is described referring to drawings.

Figure 2:
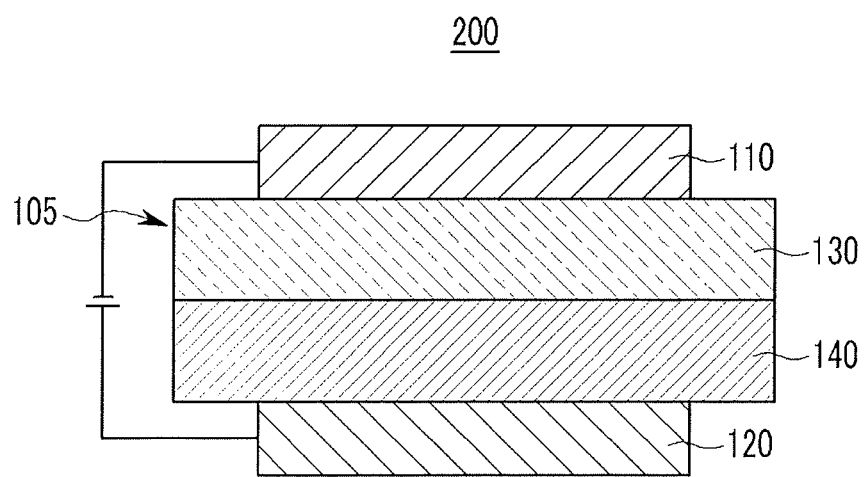

FIGS. 1 and 2 are cross-sectional views of each organic light emitting diode according to example embodiments.

Referring to FIG. 1, an organic light emitting diode 100 according to an example embodiment includes an anode 120 and a cathode 110 facing each other, and an organic layer 105 disposed between the anode 120 and cathode 110.

The anode 120 may be made of a conductor having a large work function to help hole injection, and may be for example a metal, a metal oxide and/or a conductive polymer. The anode 120 may be, for example a metal such as nickel, platinum, vanadium, chromium, copper, zinc, gold, and the like or an alloy thereof; a metal oxide such as zinc oxide, indium oxide, indium tin oxide (ITO), indium zinc oxide (IZO), and the like; a combination of a metal and an oxide such as ZnO and Al or $SnO_2$ and Sb; a conductive polymer such as poly(3-methylthiophene), poly(3,4-(ethylene-1,2-dioxy)thiophene) (PEDOT), polypyrrole, and polyaniline, etc.

The cathode 110 may be made of a conductor having a small work function to help electron injection, and may be for example a metal, a metal oxide and/or a conductive polymer. The cathode 110 may be for example a metal such as magnesium, calcium, sodium, potassium, titanium, indium, yttrium, lithium, gadolinium, aluminum, silver, tin, lead, cesium, barium, and the like, or an alloy thereof; a multi-layer structure material such as LiF/Al, $LiO_2$/Al, LiF/Ca, LiF/Al, and $BaF_2$/Ca, etc.

The organic layer 105 may include a light emitting layer 130 including a compound for the organic optoelectronic device according to an embodiment. For example, the compound for the organic optoelectronic device may be included as a phosphorescent host of the light emitting layer.

The light emitting layer may further include at least one compound, such as a dopant, for example a phosphorescent dopant, for example a red phosphorescent dopant.

The dopant may be mixed with the compound for the organic optoelectronic device in small amount to cause light emission, and may generally be a material such as a metal complex that emits light by multiple excitation into a triplet or more. The dopant may be, for example an inorganic, organic, or organic/inorganic compound, and one or more types thereof may be used.

Examples of the dopant may be a phosphorescent dopant. Examples of the phosphorescent dopant may be an organometal compound including Ir, Pt, Os, Ti, Zr, Hf, Eu, Tb, Tm, Fe, Co, Ni, Ru, Rh, Pd, or a combination thereof. The phosphorescent dopant may be for example a compound represented by Chemical Formula Z, etc.

[Chemical Formula Z]

$L^3MX$

In Chemical Formula Z, M is a metal, and $L^3$ and X are the same or different, and are a ligand to form a complex compound with M.

The M may be, for example Ir, Pt, Os, Ti, Zr, Hf, Eu, Tb, Tm, Fe, Co, Ni, Ru, Rh, Pd, or a combination thereof, and the $L^3$ and X may be, for example, bidentate ligands.

The compound for the organic optoelectronic device may be formed into a film using, for example, a dry film-forming method such as chemical vapor deposition.

Referring to FIG. 2, an organic light emitting diode 200 according to an example embodiment includes a hole auxiliary layer 140 as well as the light emitting layer 130. The hole auxiliary layer 140 may further increase hole injection and/or hole mobility between the anode 120 and the light emitting layer 130, and may block electrons. The hole auxiliary layer 140 may be, for example a hole transport layer, a hole injection layer, and/or an electron blocking layer, and may include one or more layers.

The hole auxiliary layer 140 may include, for example, at least one of compounds of Group B.

[Group B]

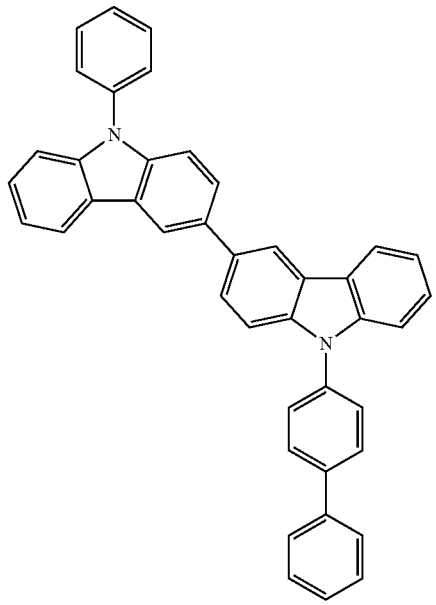

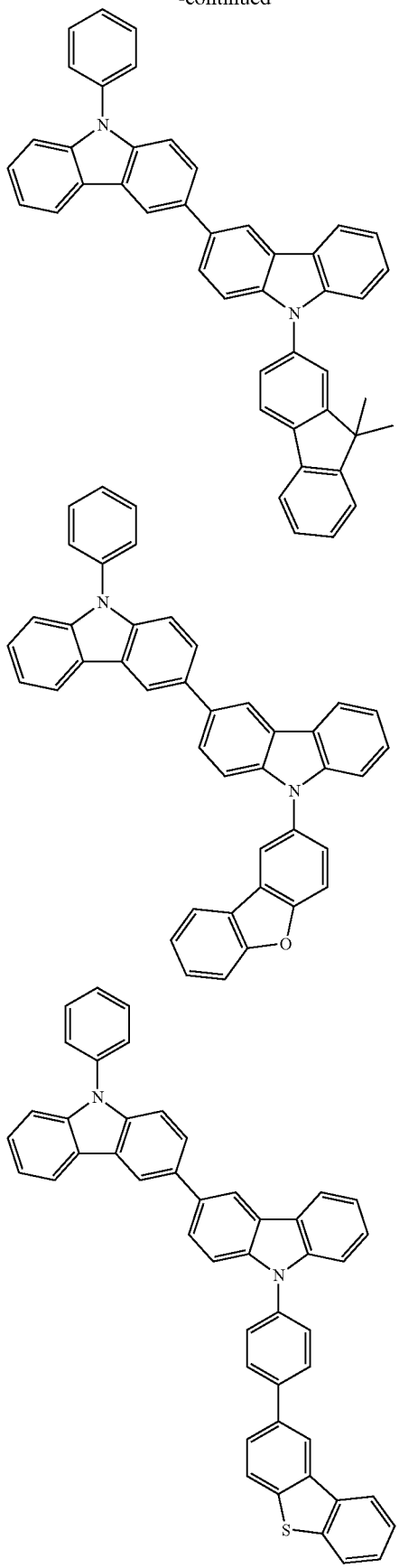
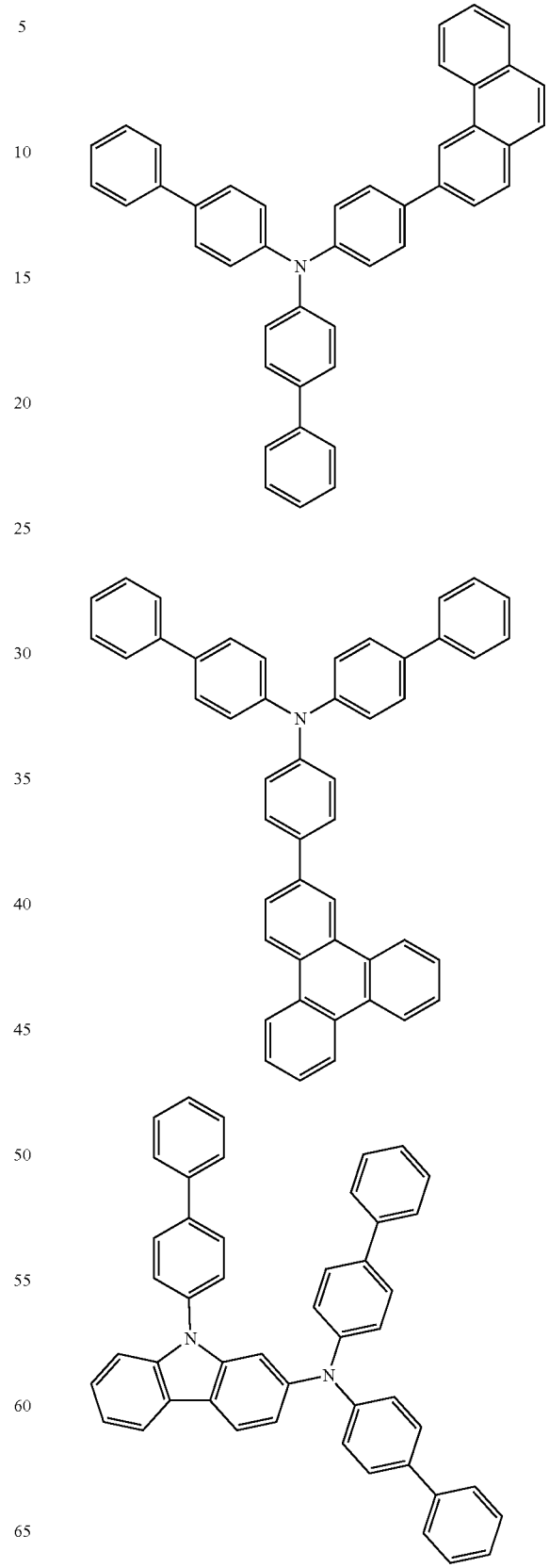

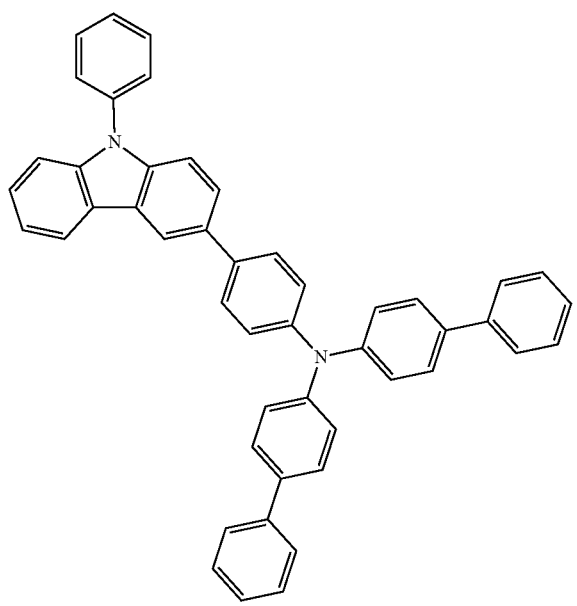
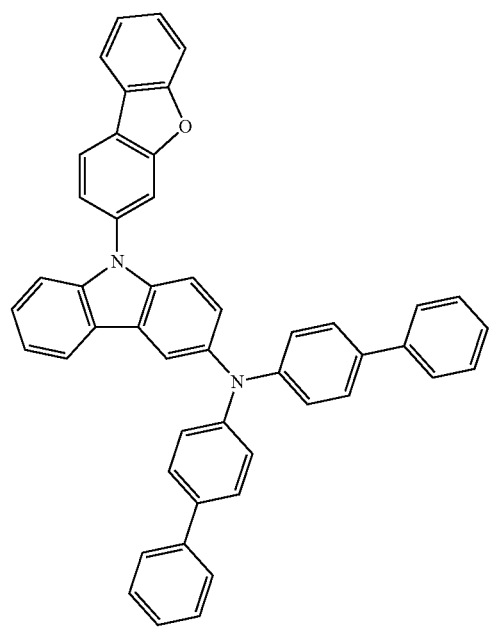
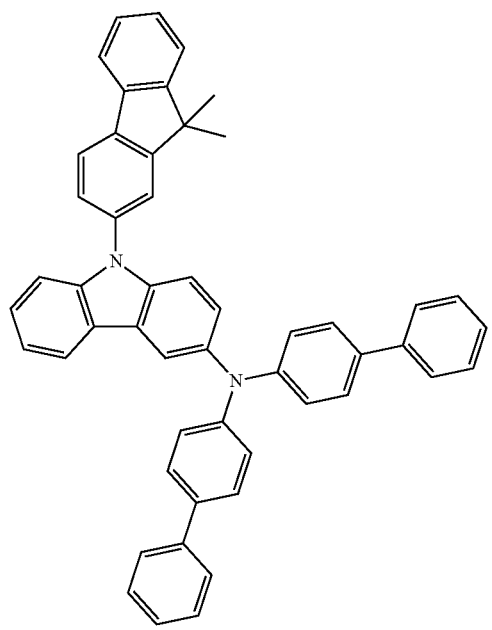
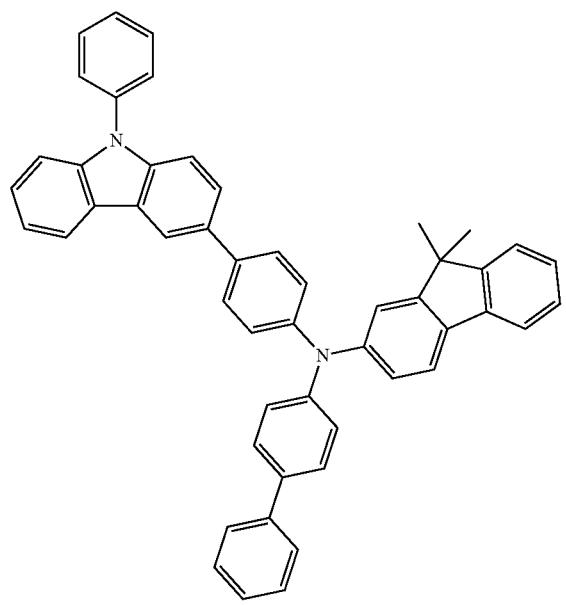

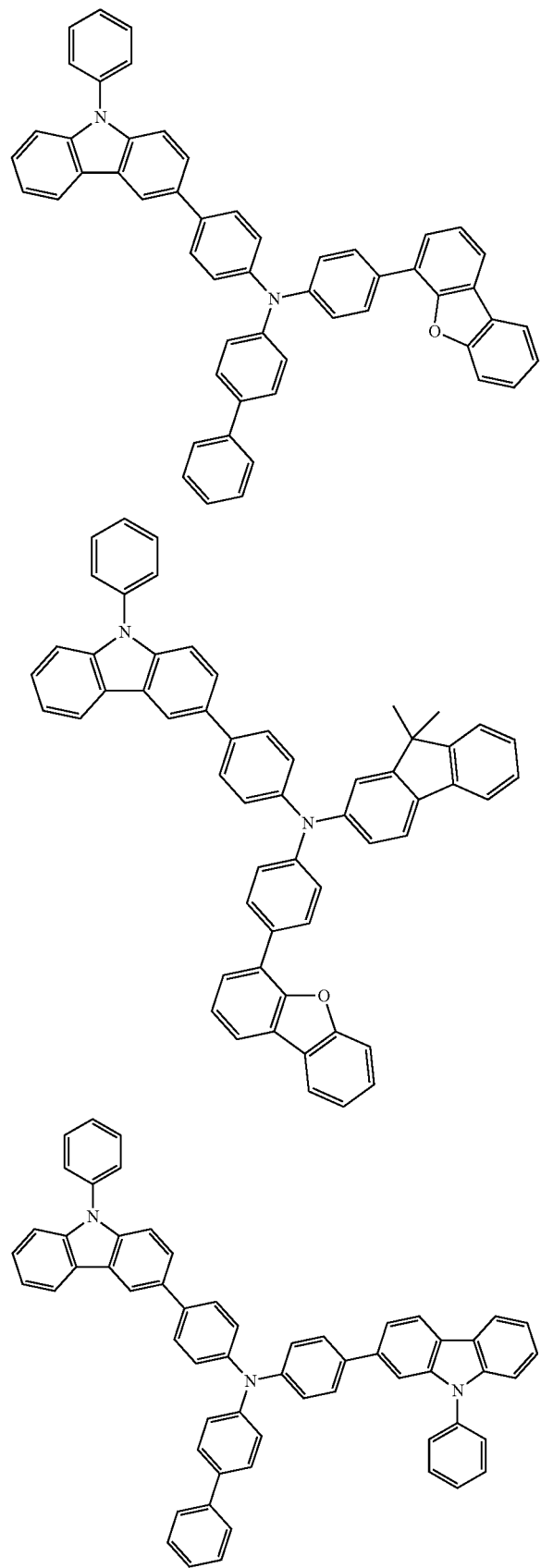
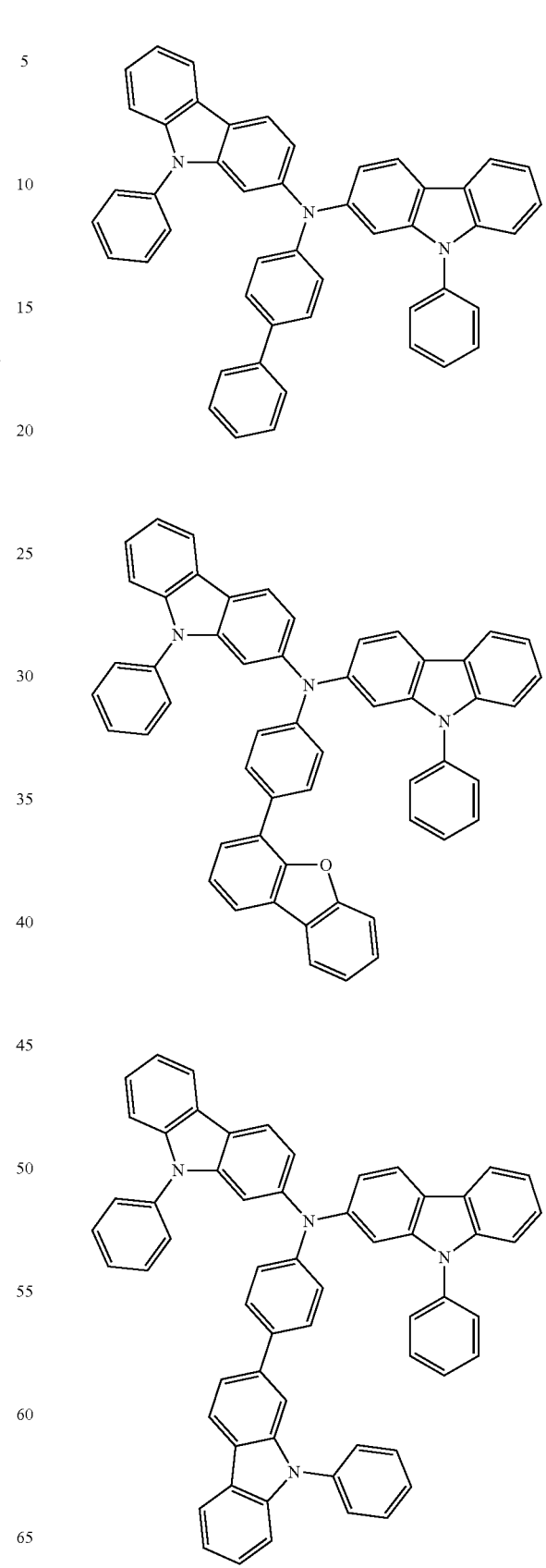

23
-continued
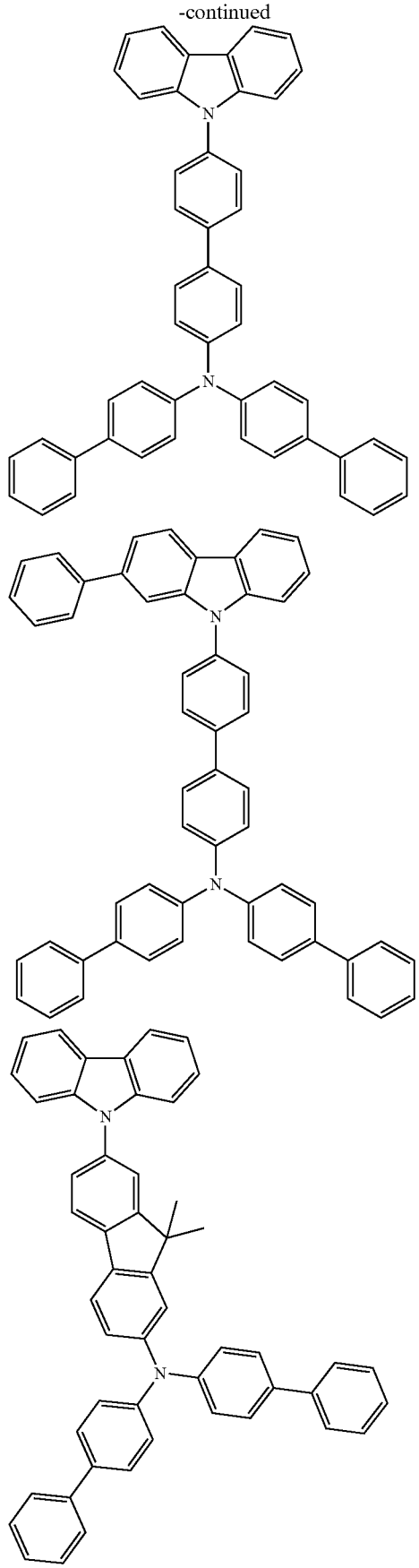
24
-continued
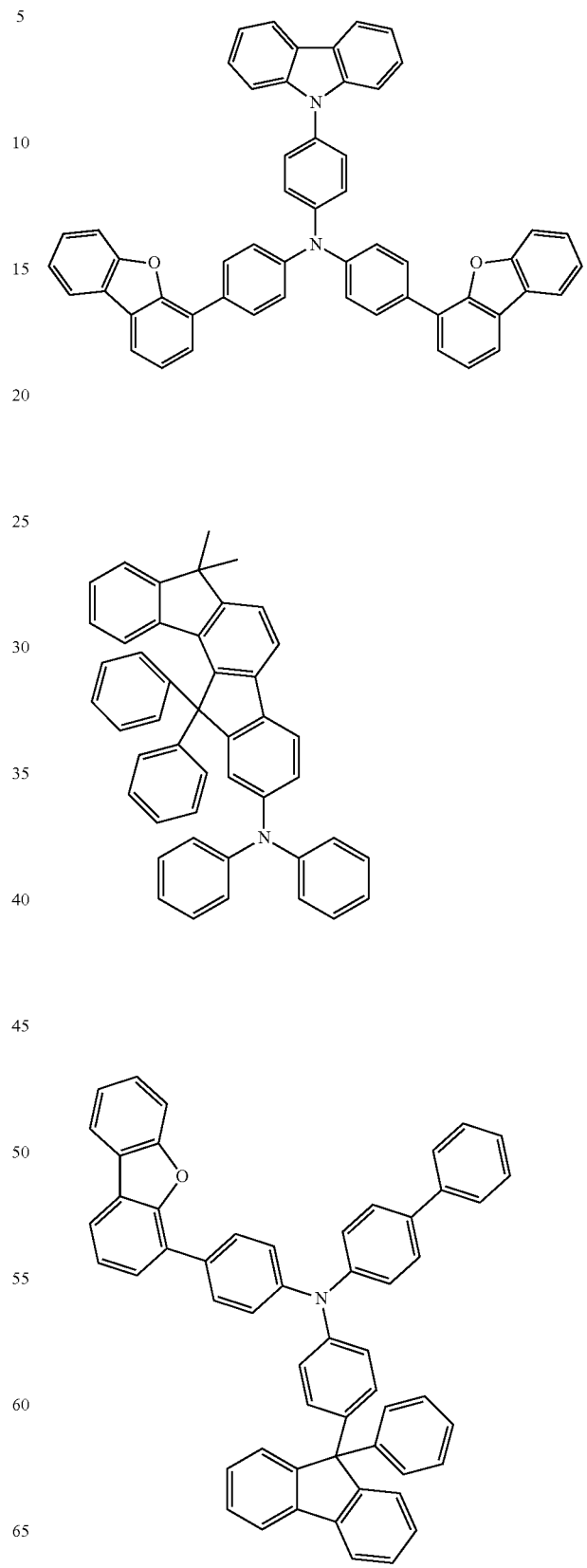

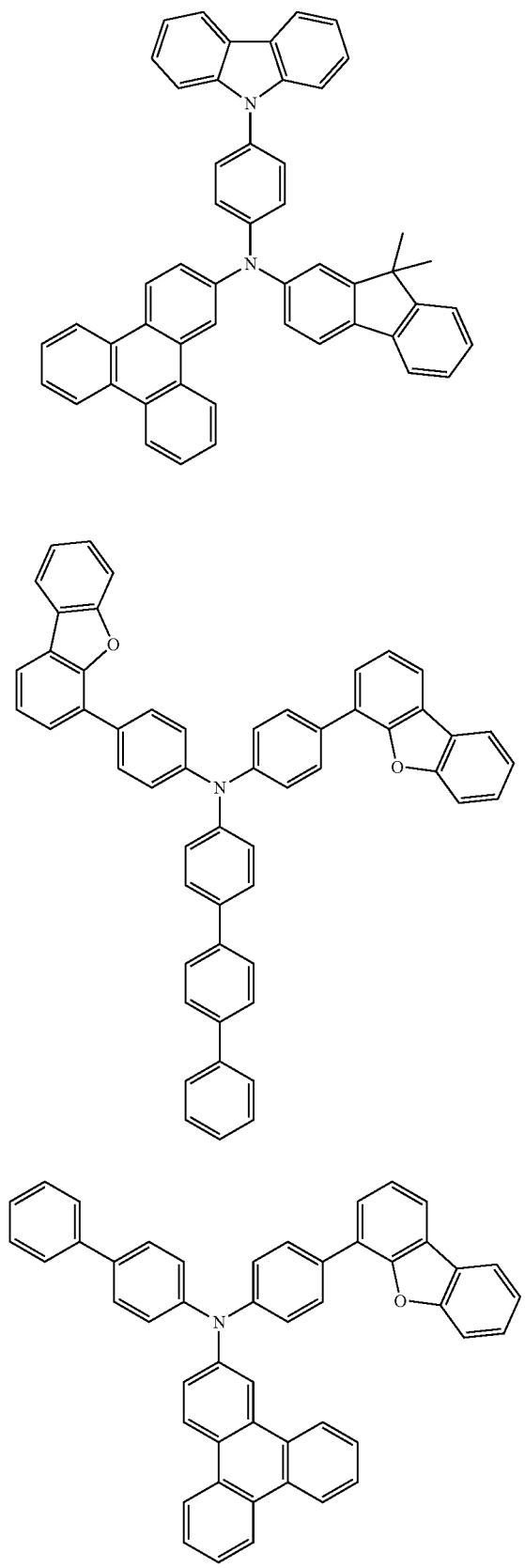
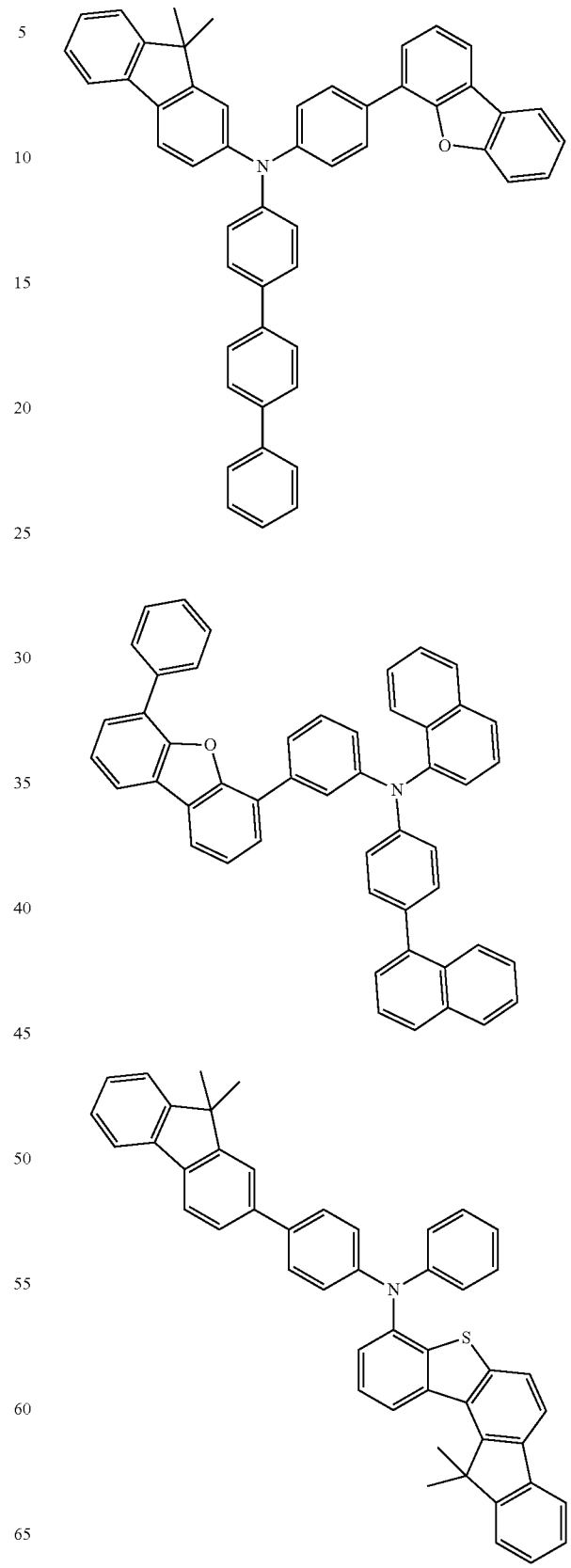

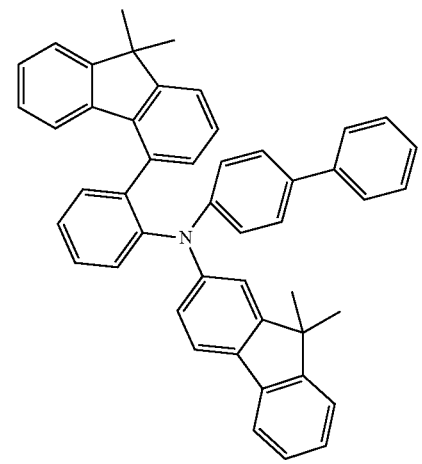
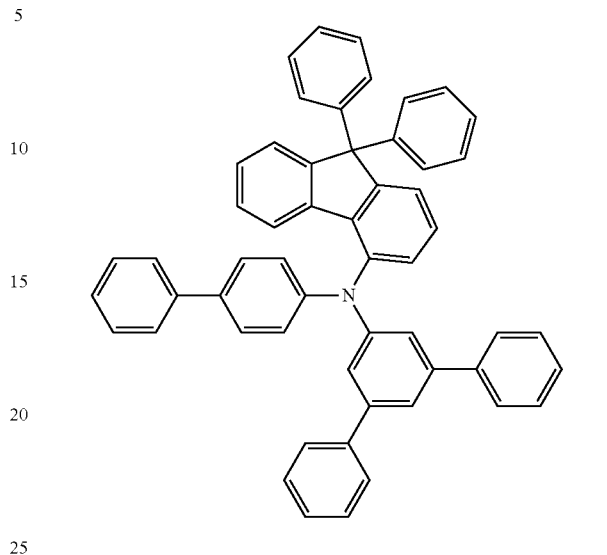
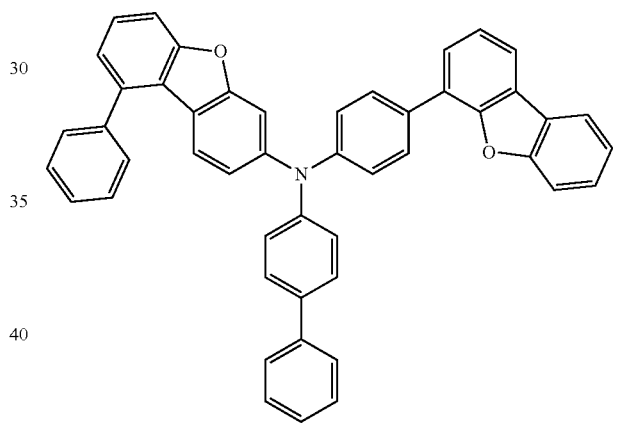
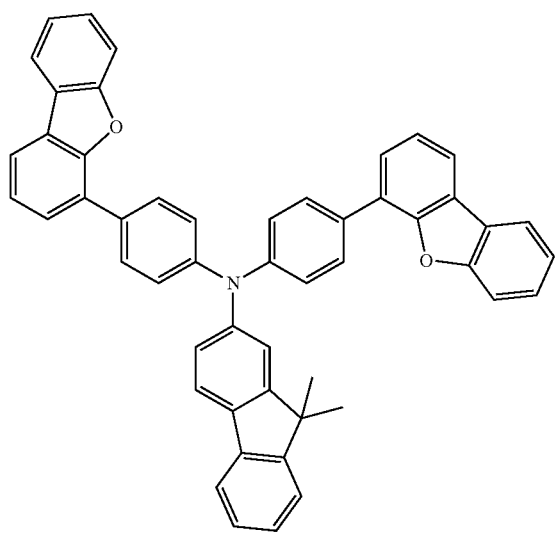
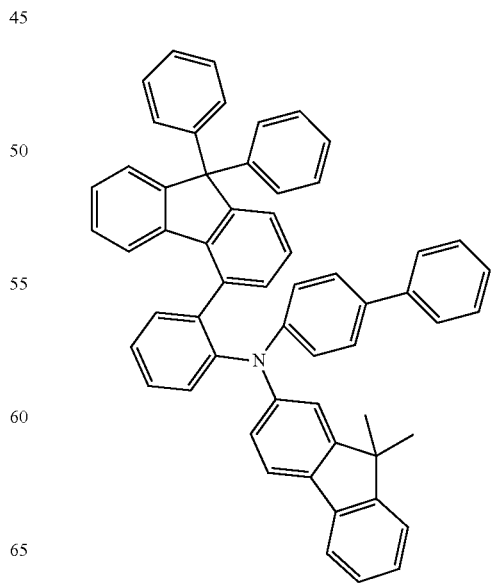
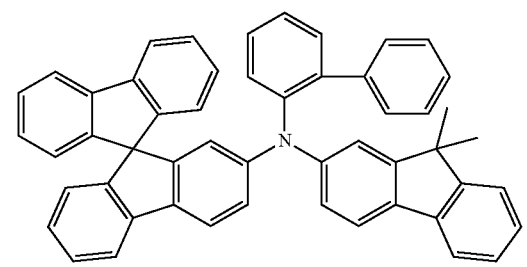

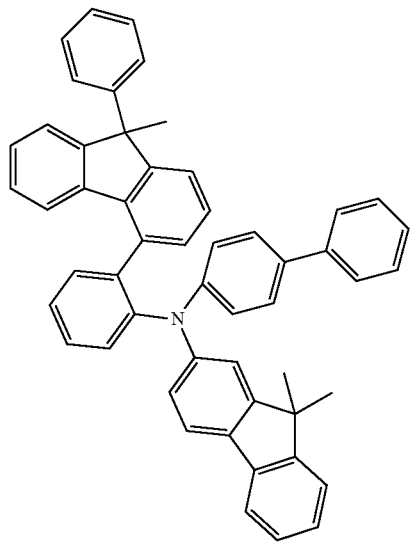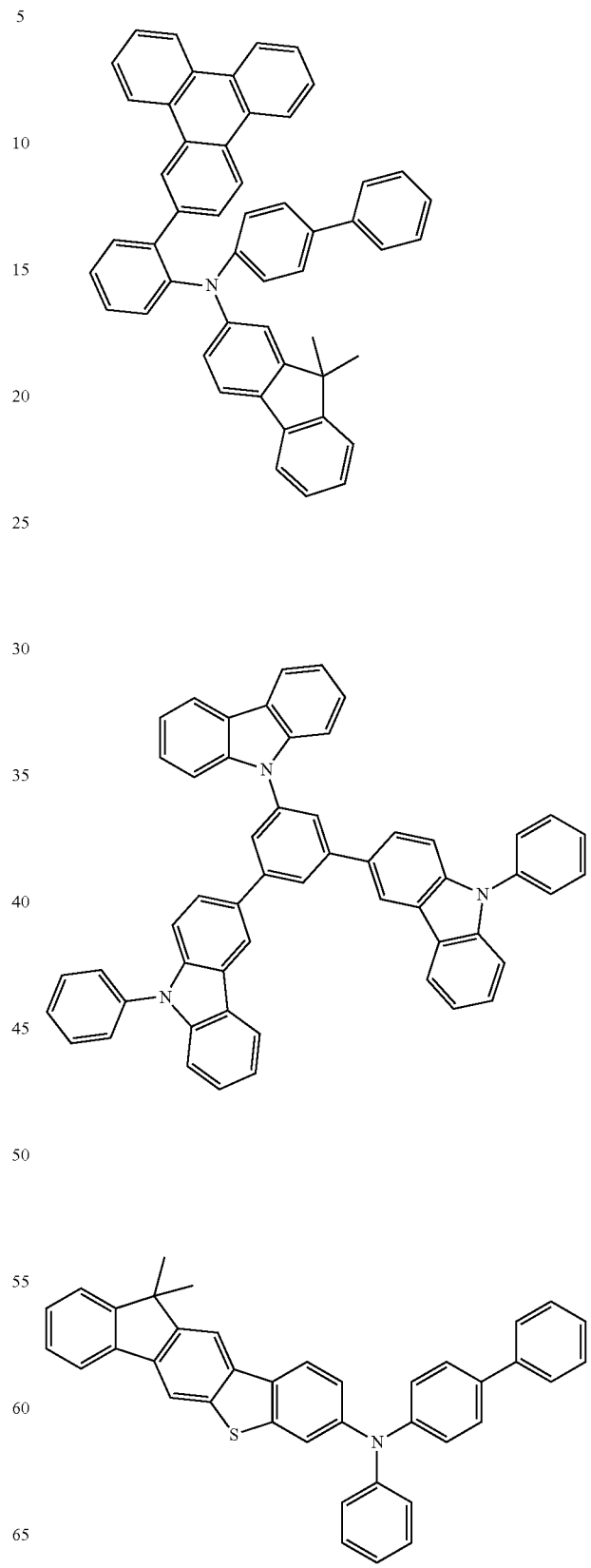

31
-continued
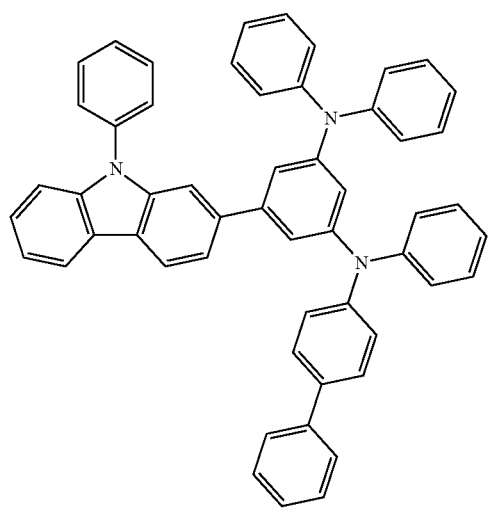
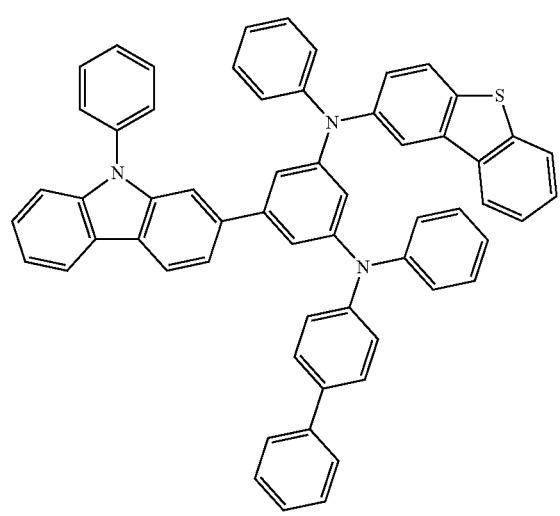
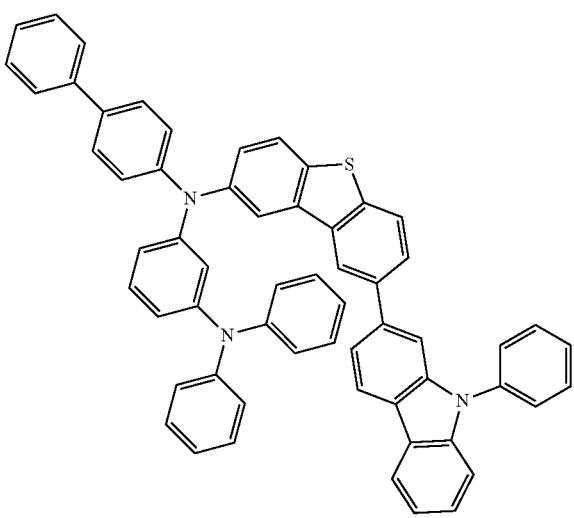
32
-continued
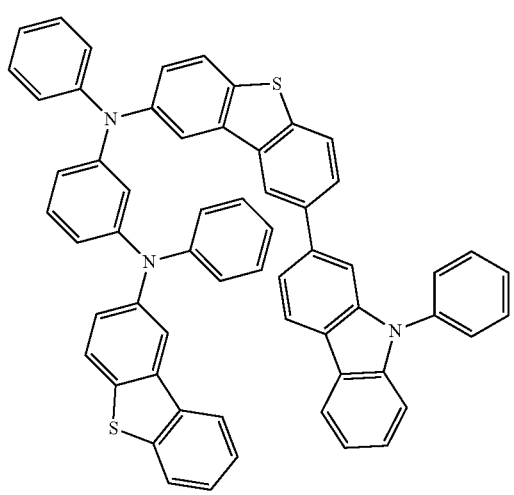
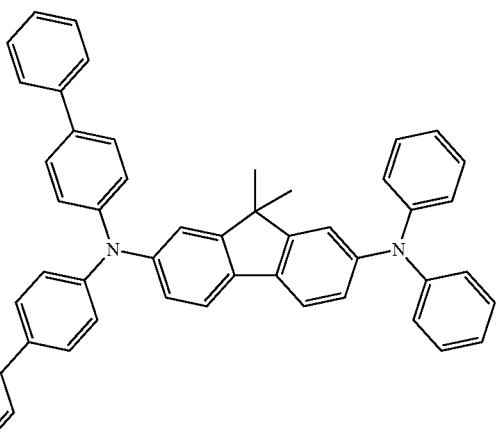

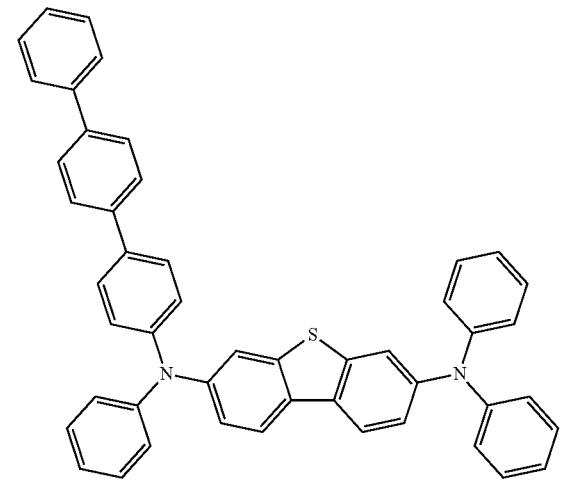
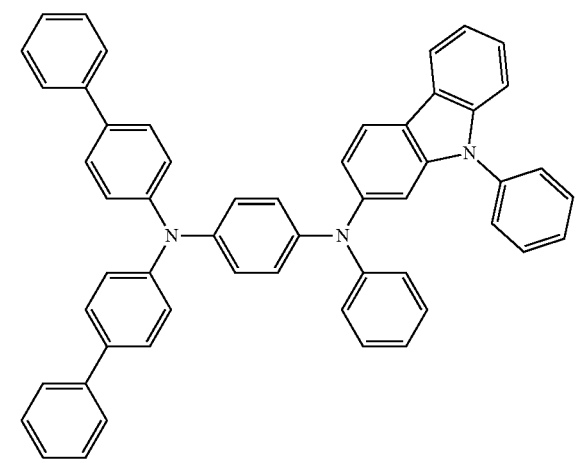
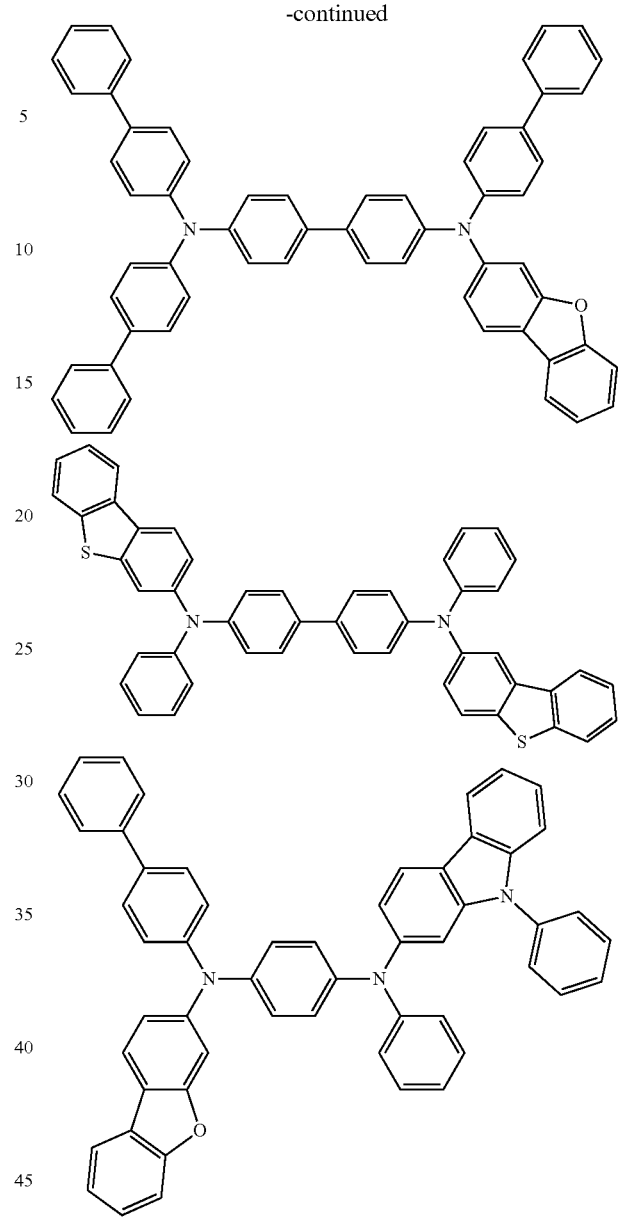
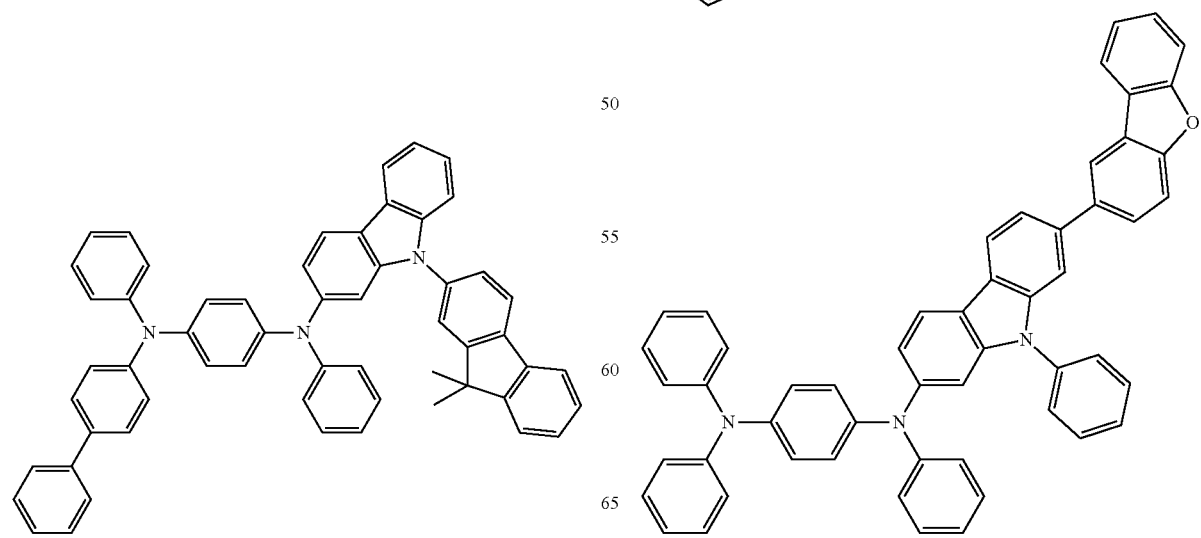

-continued
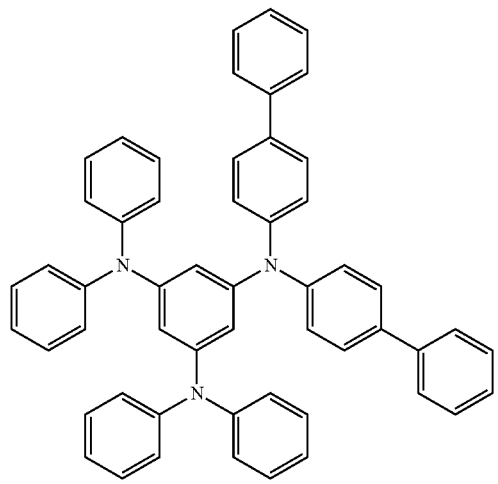
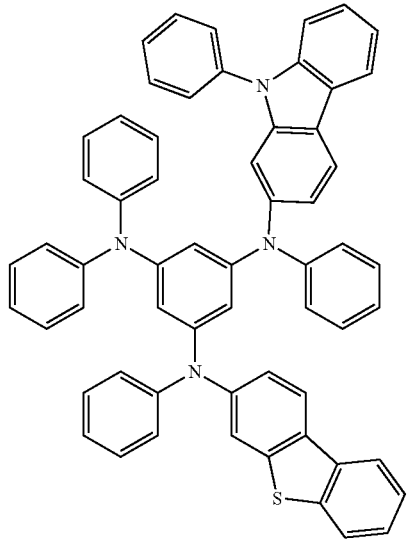
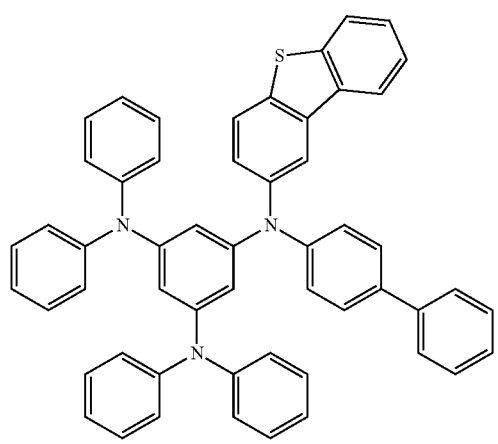
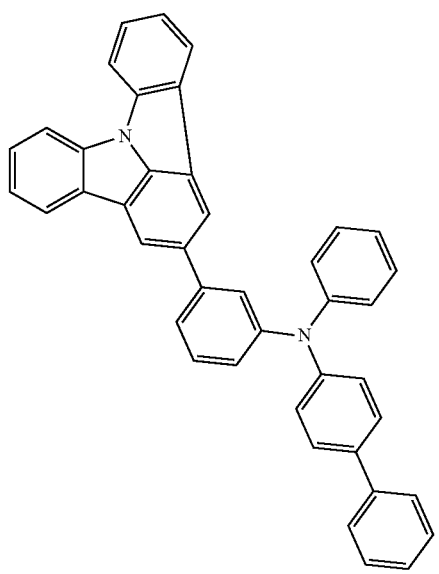
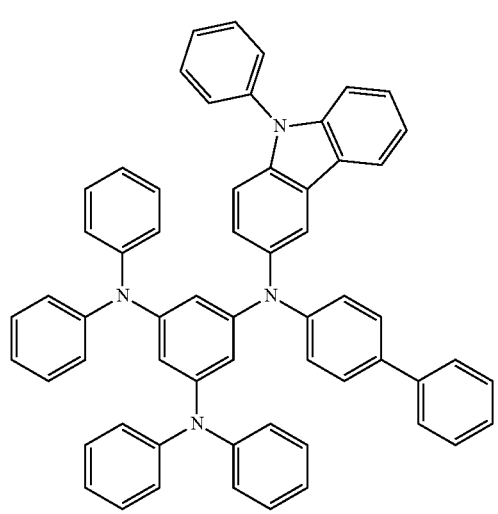
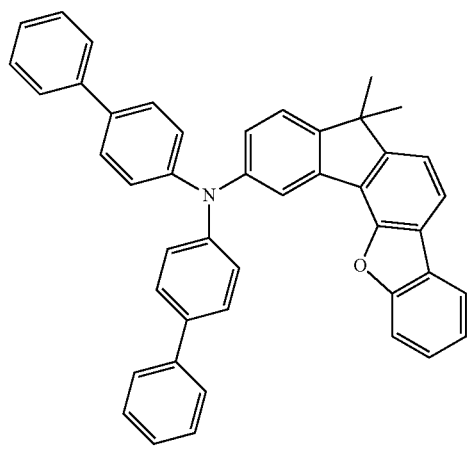

37
-continued
38
-continued
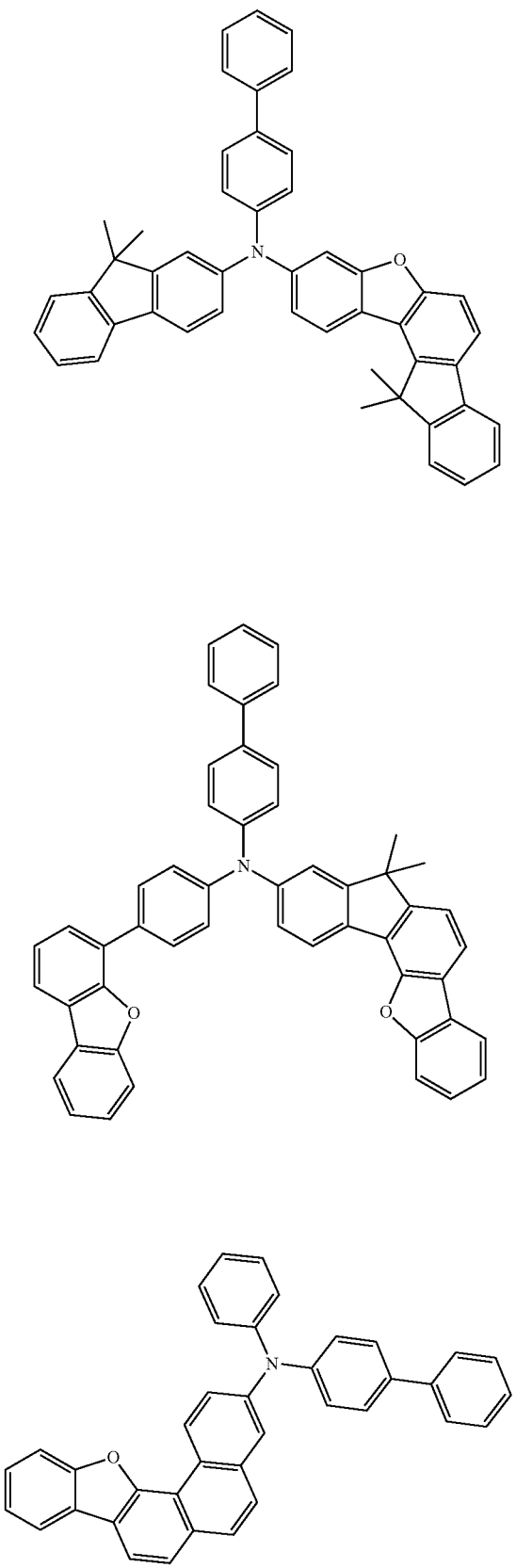
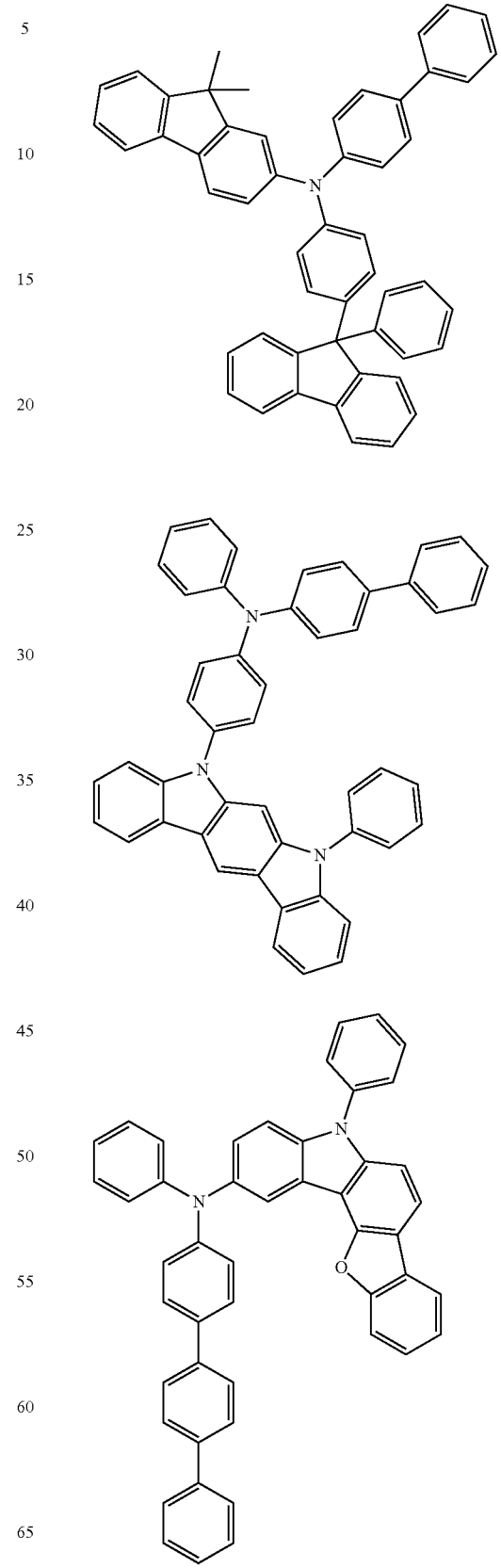

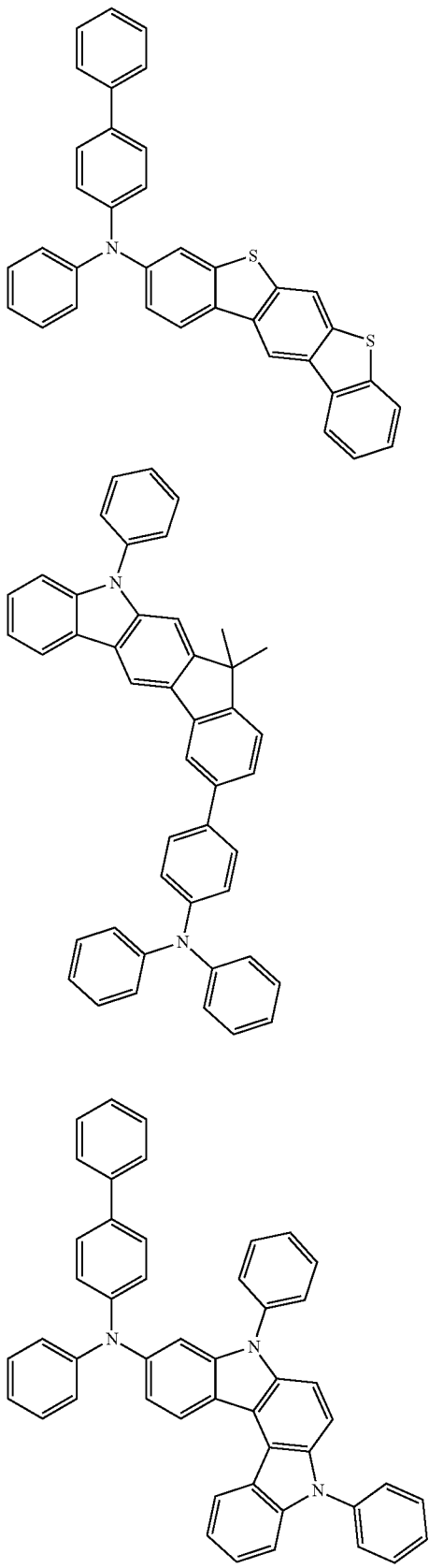

The hole auxiliary layer 140 may include a hole transport layer between the anode 120 and the light emitting layer 130 and a hole transport auxiliary layer between the light emitting layer 130 and the hole transport layer, and at least one of compounds of Group B may be included in the hole transport auxiliary layer.

In the hole transport auxiliary layer, compounds disclosed in U.S. Pat. No. 5,061,569, JP1993-009471A, WO1995-009147A1, JP1995-126615A, JP1998-095973A, and the like, and compounds similar thereto, may be used in addition to the aforementioned compounds.

In an example embodiment, in FIG. 1 or 2, an organic light emitting diode may further include an electron transport layer, an electron injection layer, or a hole injection layer in the organic layer 105.

The organic light emitting diodes 100 and 200 may be manufactured by, for example, forming an anode or a cathode on a substrate, forming an organic layer using a dry film formation method such as a vacuum deposition method (evaporation), sputtering, plasma plating, and ion plating, and forming a cathode or an anode thereon.

The organic light emitting diode may be applied to an organic light emitting display device.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

(Preparation of First Compound for Organic Optoelectronic Device)

Synthesis Example 1: Synthesis of Compound A-1

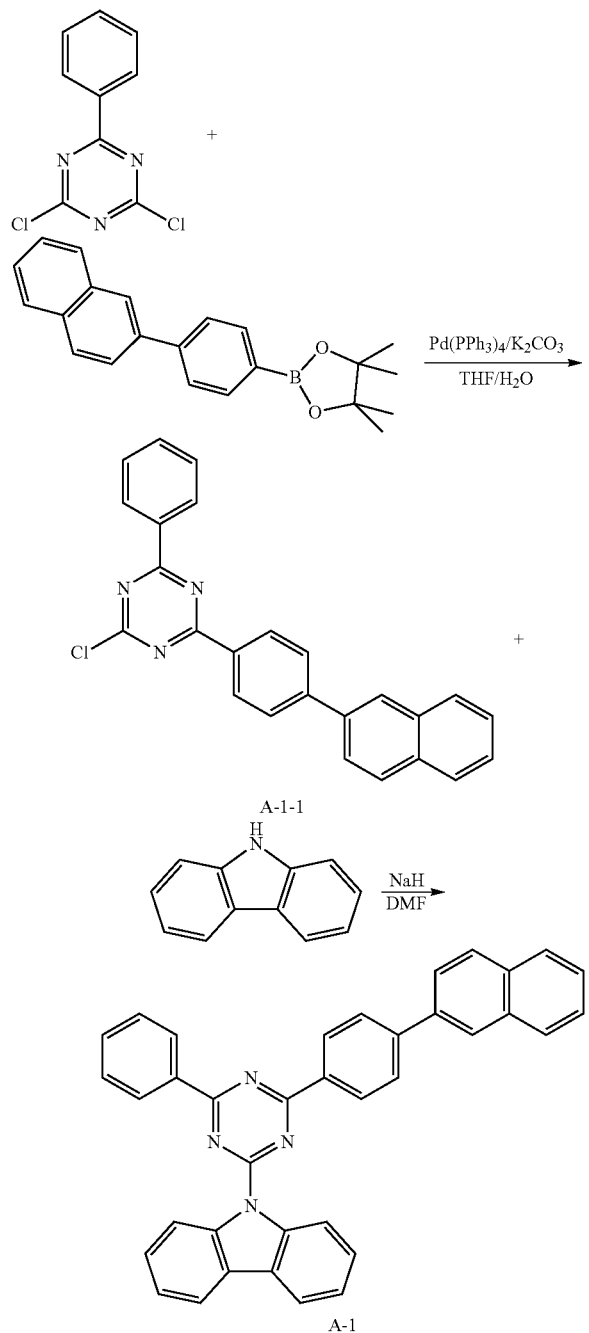

a) Synthesis of Intermediate A-1-1

2,4-Dichloro-6-phenyl-1,3,5-triazine (21.0 g, 93.12 mmol), 4,4,5,5-tetramethyl-2-(4-naphthalen-2-yl-phenyl)-[1,3,2]dioxaborolane (20.5 g, 62.08 mmol), tetrakis(triphenylphosphine)palladium (2.1 g, 1.86 mmol), and potassium carbonate (17.1 g, 124.16 mmol) were put in a round-bottomed flask and dissolved in 200 mL of tetrahydrofuran and 100 mL of distilled water and then heated and refluxed under a nitrogen atmosphere. After 6 hours, the reaction solution was cooled down, and after removing an aqueous layer therefrom, an organic layer therein was dried under a reduced pressure. The obtained solid was washed with water and methanol and recrystallized with 400 mL of toluene to obtain 18.0 g (yield of 74%) of Intermediate A-1-1.

b) Synthesis of Compound A-1

Intermediate A-1-1 (22.5 g 57.2 mmol) and carbazole (7.9 g, 47.6 mmol) were dissolved in 200 mL of DMF, and NaH was added thereto. After stirred the mixture at room temperature for 4 hours, the reaction solution was added to 500 mL of water to form a precipitate. A solid formed therein was filtered and then washed with water and methanol. The obtained solid was recrystallized in 500 mL of chlorobenzene to obtain 22.8 g (91%) of Compound A-1.

LC/MS calculated for: C37H24N4 Exact Mass: 524.20 found for 524.25 [M+H].

Synthesis Example 2: Synthesis of Compound A-3

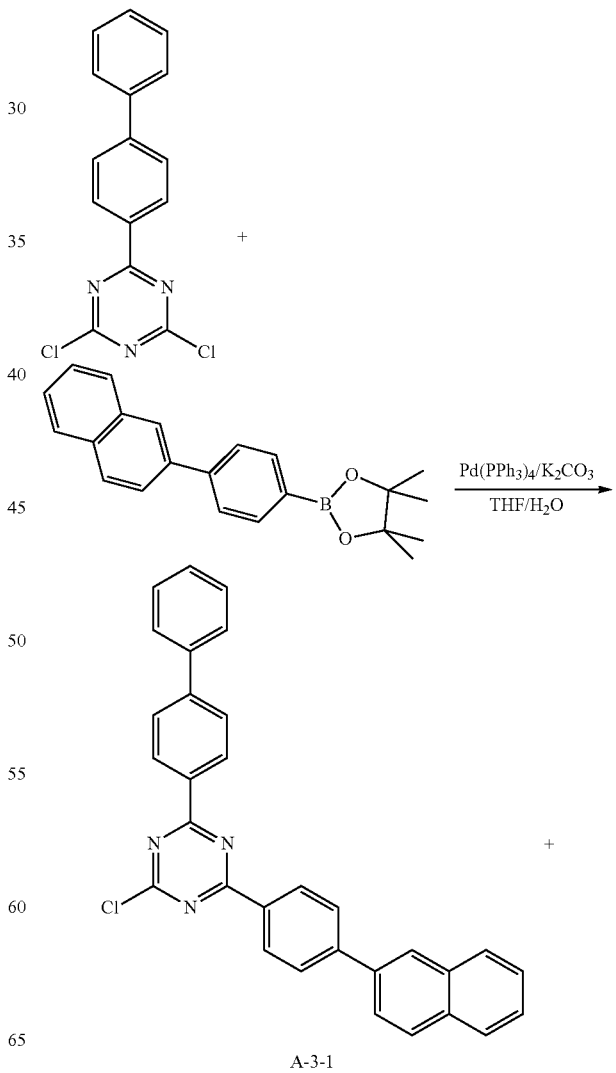

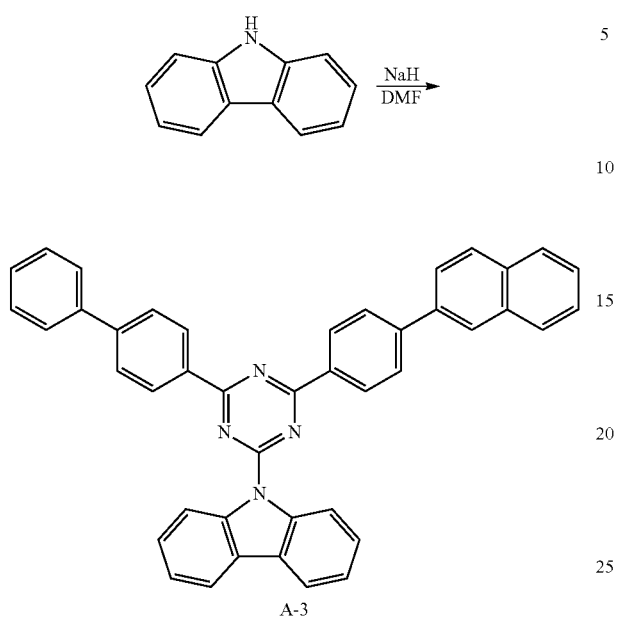

A-3 a) Synthesis of Intermediate A-3-1

15.0 g (61%) of Intermediate A-3-1 was synthesized according to the same method as the a) of Synthesis Example 1 except that 2-biphenyl-4-yl-4,6-dichloro-[1,3,5]triazine (28.14 g, 93.15 mmol) and 4,4,5,5-tetramethyl-2-(4-naphthalen-1-yl-phenyl)-[1,3,2]dioxaborolane (20.5 g, 62.08 mmol) were used.

b) Synthesis of Compound A-3

25.0 g (83%) of Compound A-3 was synthesized according the same method as the b) of Synthesis Example 1 except that Intermediate A-3-1 (26.9 g 57.19 mmol) and carbazole (9.5 g, 57.2 mmol) were used.

LC/MS calculated for: C43H28N4 Exact Mass: 600.23 found for 600.28 [M+H].

Synthesis Example 3: Synthesis of Compound A-17

[Reaction Scheme 3]

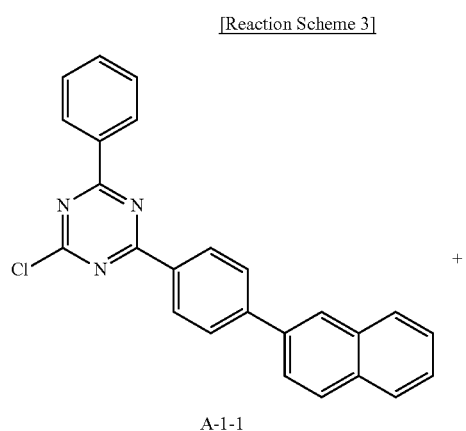

A-1-1

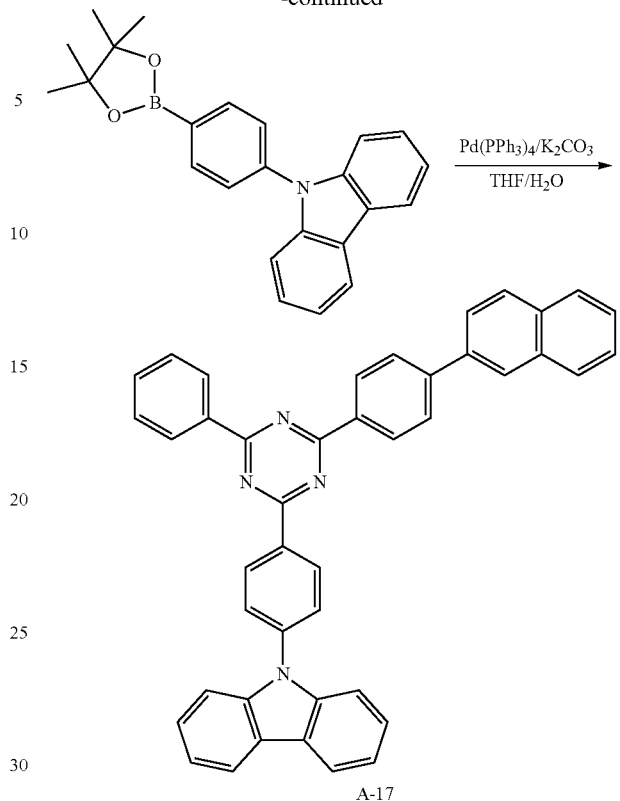

A-17

Intermediate A-1-1 (20.0 g, 50.78 mmol), 9-[4-(4,4,5,5-tetramethyl-[1,3,2]dioxaborolan-2-yl)-phenyl]-9H-carbazole (22.5 g, 60.93 mmol), and tetrakis(triphenylphosphine) palladium (1.7 g, 1.52 mmol), and potassium carbonate (14.0 g, 101.56 mmol) were dissolved in 300 mL of tetrahydrofuran and 150 mL of distilled water in a round-bottomed flask and then, heated and refluxed under a nitrogen atmosphere. After 12 hours, the reaction solution was cooled down and, after removing an aqueous layer therefrom, an organic layer therein was dried under a reduced pressure. The obtained solid was washed with water and methanol and then recrystallized with 600 mL of monochlorobenzene to obtain 27.5 g (yield of 90%) of Compound A-17.

LC/MS calculated for: C43H28N4 Exact Mass: 600.23 found for 600.27 [M+H].

Synthesis Example 4: Synthesis of Compound A-18

[Reaction Scheme 4]

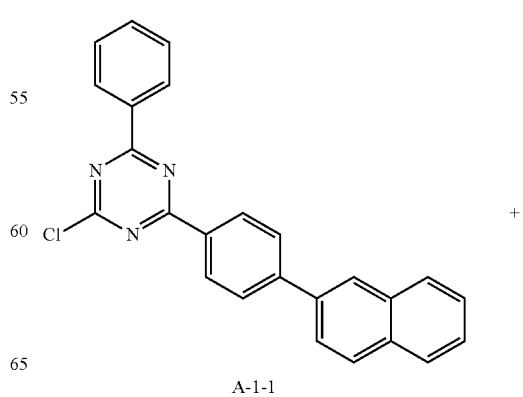

A-1-1

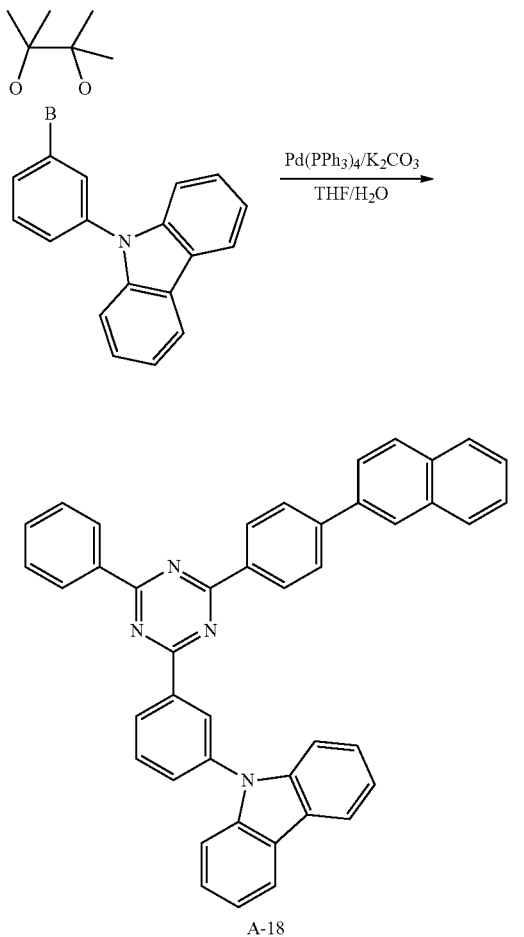

A-18

13.9 g (91%) of Compound A-18 was synthesized according to the same method as Synthesis Example 3 except that Intermediate A-1-1 (10.0 g, 25.39 mmol) and 9-[3-(4,4,5,5-tetramethyl-[1,3,2]dioxaborolan-2-yl)-phenyl]-9H-carbazole (11.2 g, 30.47 mmol) were used.

LC/MS calculated for: C43H28N4 Exact Mass: 600.23 found for 600.27 [M+H].

Synthesis Example 5: Synthesis of Compound A-19

[Reaction Scheme 5]

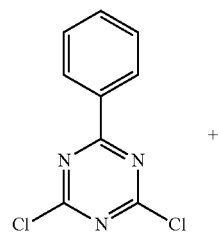

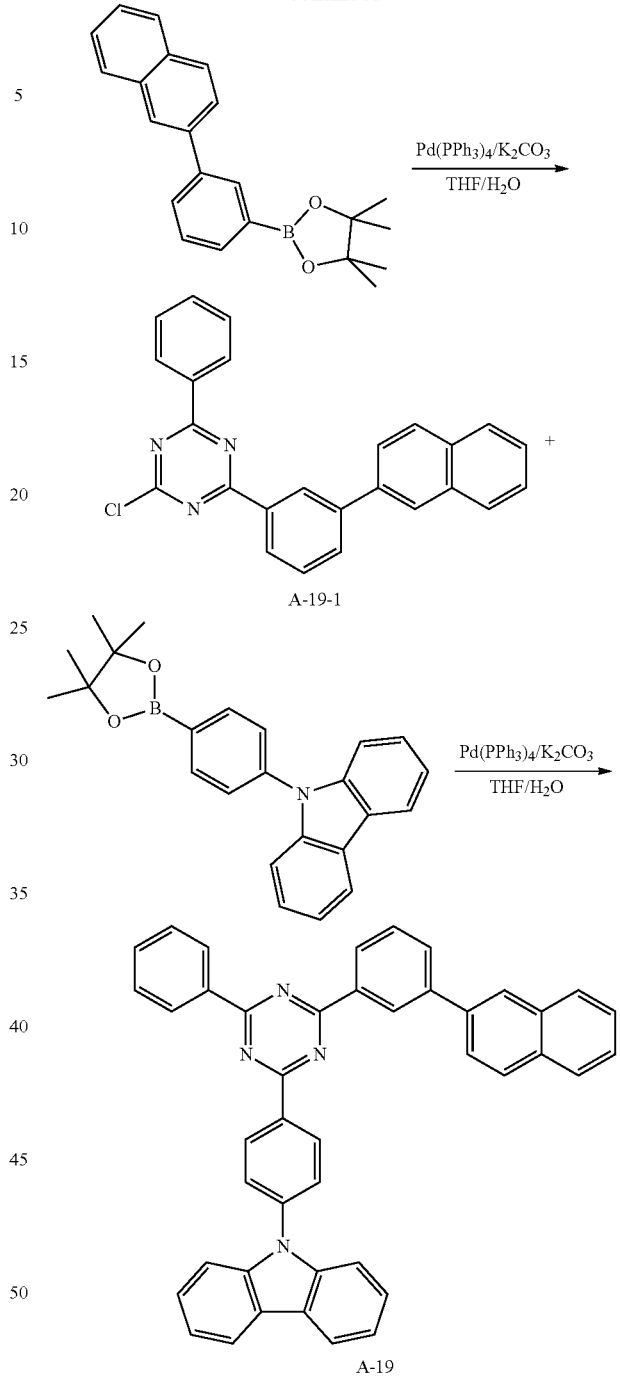

A-19 a) Synthesis of Intermediate A-19-1

12.0 g (49%) of Intermediate A-19-1 were synthesized according to the same method as the a) of Synthesis Example 1 except that 2,4-dichloro-6-phenyl-1,3,5-triazine (21.1 g, 93.12 mmol) and 4,4,5,5-tetramethyl-2-(3-naphthalen-1-yl-phenyl)-[1,3,2]dioxaborolane (20.5 g, 62.08 mmol) were used.

b) Synthesis of Compound A-19

13.9 g (91%) of Compound A-19 were synthesized according the same method as Synthesis Example 3 except that Intermediate A-19-1 (10.0 g, 25.39 mmol) and 9-[4-(4,4,5,5-tetramethyl-[1,3,2]dioxaborolan-2-yl)-phenyl]-9H-carbazole (11.2 g, 30.47 mmol) were used.

LC/MS calculated for: C43H28N4 Exact Mass: 600.23 found for 600.28 [M+H].

Comparative Synthesis Example 1: Synthesis of Compound Y-1

[Reaction Scheme 6]

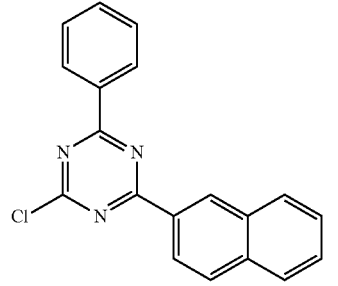

+

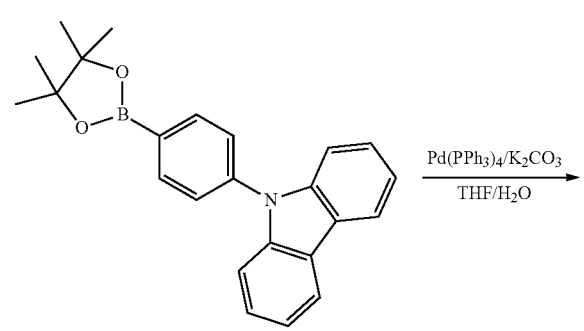

Pd(PPh3)4/K2CO3
THF/H2O
→

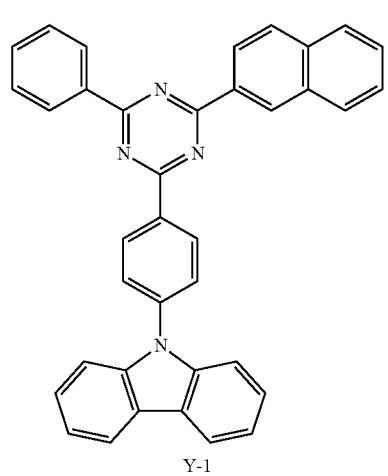

Y-1

15.0 g (91%) of Compound Y-1 was synthesized according to the same method as Synthesis Example 3 except that an intermediate of 2-chloro-4-naphthalen-2-yl-6-phenyl-[1,3,5]triazine (10.0 g, 31.47 mmol) and 9-[4-(4,4,5,5-tetramethyl-[1,3,2]dioxaborolan-2-yl)-phenyl]-9H-carbazole (11.6 g, 31.47 mmol) were used.

LC/MS calculated for: C37H24N4 Exact Mass: 524.20 found for 524.27 [M+H].

Comparative Synthesis Example 2: Synthesis of Compound Y-2

[Reaction Scheme 7]

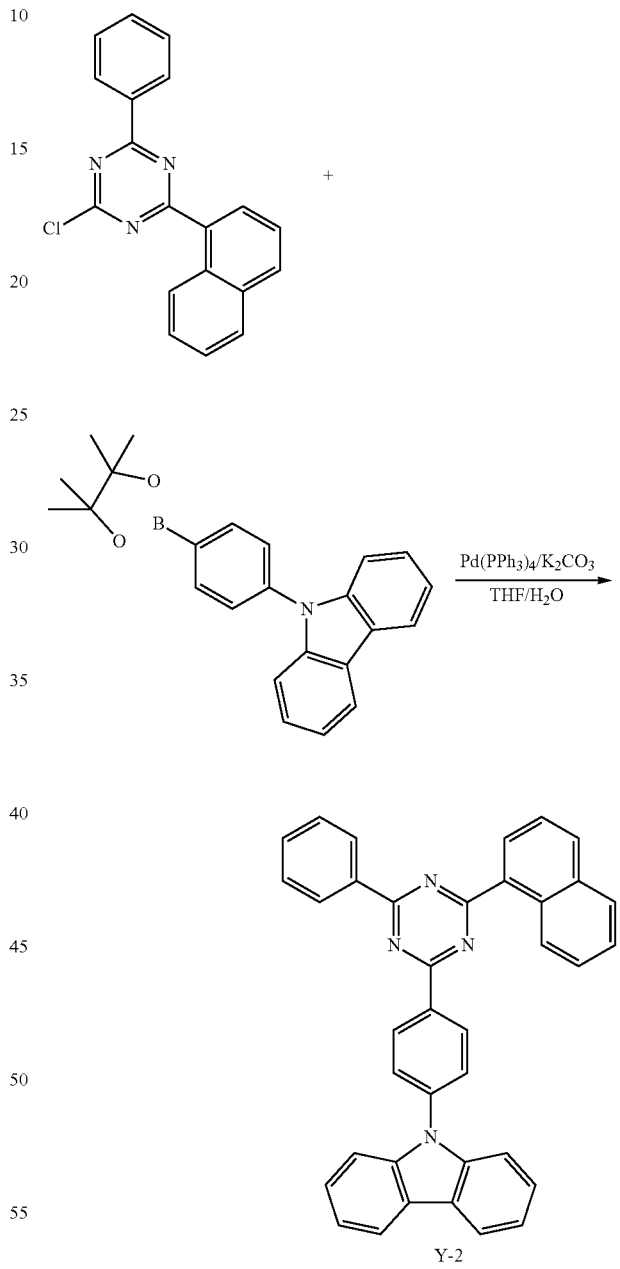

18.0 g (73%) of Compound Y-2 were synthesized according to the same method as Synthesis Example 3 except that 2-chloro-4-naphthalen-1-yl-6-phenyl-[1,3,5]triazine (15.0 g, 47.20 mmol) and 9-[4-(4,4,5,5-tetramethyl-[1,3,2]dioxaborolan-2-yl)-phenyl]-9H-carbazole (17.4 g, 47.20 mmol) were used.

LC/MS calculated for: C37H24N4 Exact Mass: 524.20 found for 524.25 [M+H].

Comparative Synthesis Example 3: Synthesis of Compound Y-3

[Reaction Scheme 8]

a) Synthesis of Intermediate Y-3-1

17.0 g (49%) of Intermediate Y-3-1 were synthesized according to the same method as the a) of Synthesis Example 1 except that an intermediate of 2,4-dichloro-6-phenyl-1,3,5-triazine (20.0 g, 88.47 mmol) and 4,4,5,5-tetramethyl-2-(4-naphthalen-1-yl-phenyl)-[1,3,2]dioxaborolane (27.76 g, 84.05 mmol) were used.

b) Synthesis of Compound Y-3

15.0 g (82%) of Intermediate Y-3 were synthesized according to the same method as Synthesis Example 3 except that Intermediate Y-3-1 (12.0 g, 30.47 mmol) and 9-[4-(4,4,5,5-tetramethyl-[1,3,2]dioxaborolan-2-yl)-phenyl]-9H-carbazole (13.5 g, 35.56 mmol) were used.

LC/MS calculated for: C43H28N4 Exact Mass: 600.23 found for 600.28 [M+H].

Comparative Synthesis Example 4: Synthesis of Compound Y-4

[Reaction Scheme 9]

-continued

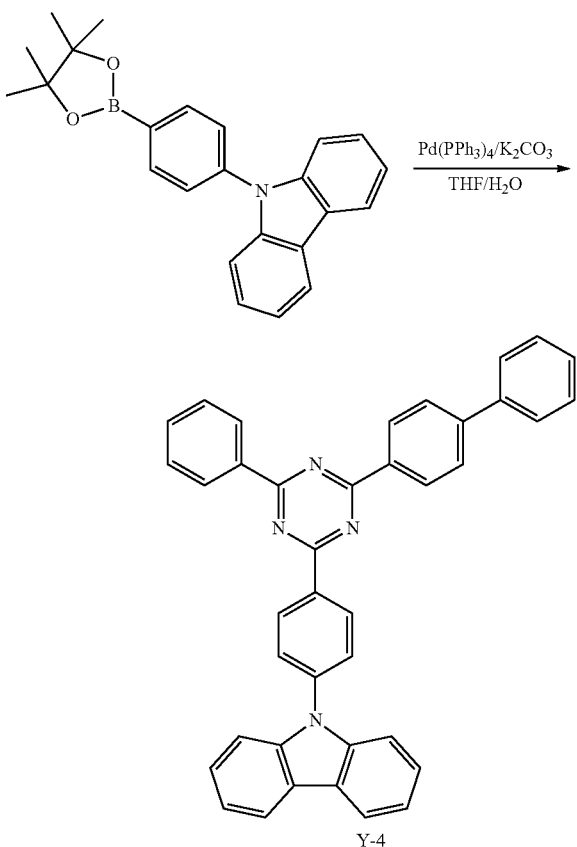

Y-4

12.0 g (75%) of Intermediate Y-4 were synthesized according to the same method as Synthesis Example 3 except that 2-biphenyl-4-yl-4-chloro-6-phenyl-[1,3,5]triazine (10.0 g, 29.09 mmol) and 9-[4-(4,4,5,5-tetramethyl-[1,3,2]dioxaborolan-2-yl)-phenyl]-9H-carbazole (12.9 g, 34.90 mmol) were used.

LC/MS calculated for: C39H26N4 Exact Mass: 550.22 found for 550.27 [M+H].

Comparative Synthesis Example 5: Synthesis of Compound Y-5

[Reaction Scheme 10]

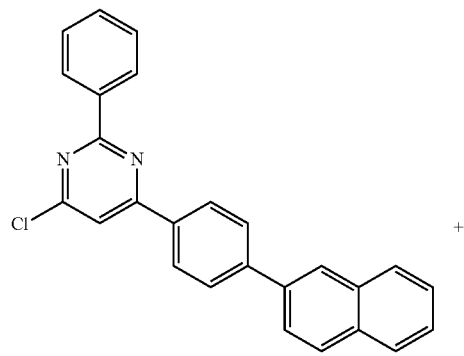

+

-continued

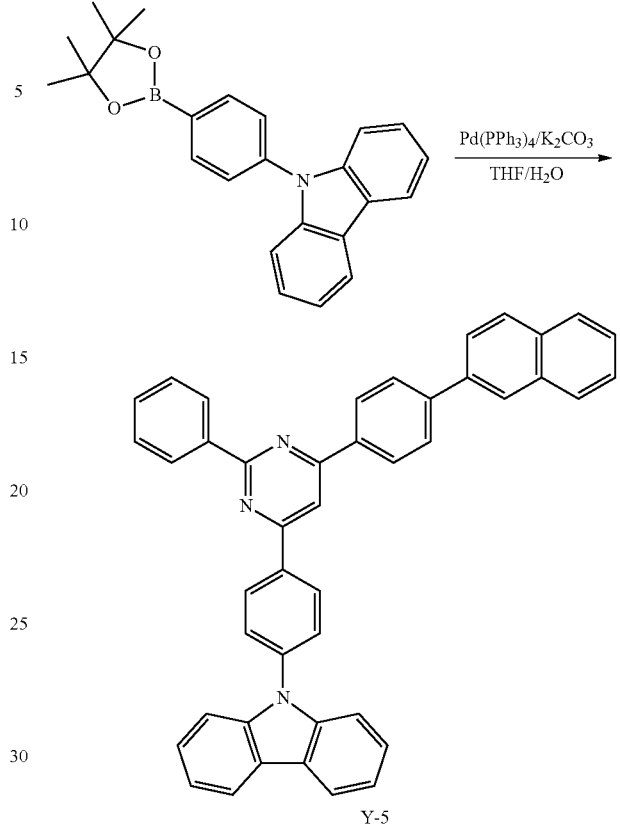

Y-5

10.0 g (66%) of Compound Y-5 were synthesized according to the same method as Synthesis Example 3 except that an intermediate of 4-chloro-6-(4-naphthalen-2-yl-phenyl)-2-phenyl-pyrimidine (10.0 g, 25.45 mmol) and 9-[4-(4,4,5,5-tetramethyl-[1,3,2]dioxaborolan-2-yl)-phenyl]-9H-carbazole (11.28 g, 30.54 mmol) were used.

LC/MS calculated for: C44H29N3 Exact Mass: 599.24 found for 599.29 [M+H].

(Manufacture of Organic Light Emitting Diode)

Example 1

A glass substrate coated with ITO (indium tin oxide) as a 1500 Å-thick thin film was washed with distilled water. After washing with the distilled water, the glass substrate was ultrasonic wave-washed with a solvent such as isopropyl alcohol, acetone, methanol, and the like and dried and then, moved to a plasma cleaner, cleaned by using oxygen plasma for 10 minutes, and moved to a vacuum depositor. This obtained ITO transparent electrode was used as an anode, Compound A was vacuum-deposited on the ITO substrate to form a 700 Å-thick hole injection layer, and Compound B was deposited to be 50 Å-thick on the hole injection layer, and then Compound C was deposited to be 700 Å-thick to form a hole transport layer. On the hole transport layer, Compound C-1 was vacuum-deposited to be a 400 Å-thick to form a hole transport auxiliary layer. On the hole transport auxiliary layer, 400 Å-thick light emitting layer was formed by using Compound A-1 as a host and doping 2 wt % of [Ir(piq)$_2$acac] as a dopant by a vacuum-deposition. Subsequently, on the light emitting layer, a 300 Å-thick electron transport layer was formed by simultaneously vacuum-depositing Compound D and Liq in a ratio of 1:1, and on the electron transport layer, Liq and Al were sequentially vacuum-deposited to be 15 Å-thick and 1200 Å-thick. An organic light emitting diode was thus manufactured.

The organic light emitting diode had a five-layered organic thin layer of the following structure.

ITO/Compound A (700 Å)/Compound B (50 Å)/Compound C (700 Å)/Compound C-1 (400 Å)/EML [Compound A-1: [Ir(piq)$_2$acac] (2 wt %)] (400 Å)/Compound D: Liq (300 Å)/Liq (15 Å)/Al (1200 Å).

Compound A: N4,N4'-diphenyl-N4,N4'-bis(9-phenyl-9H-carbazol-3-yl)biphenyl-4,4'-diamine Compound B: 1,4,5,8,9,11-hexaazatriphenylene-hexacarbonitrile (HAT-CN)

Compound C: N-(biphenyl-4-yl)-9,9-dimethyl-N-(4-(9-phenyl-9H-carbazol-3-yl)phenyl)-9H-fluoren-2-amine Compound C-1: N,N-di([1,1'-biphenyl]-4-yl)-7,7-dimethyl-7H-fluoreno[4,3-b]benzofuran-10-amine Compound D: 8-(4-(4,6-di(naphthalen-2-yl)-1,3,5-triazin-2-yl)phenyl)quinoline Examples 2 to 5

Each organic light emitting diode was manufactured according to the same method as Example 1 except that the host compounds were changed as in Table 1.

Comparative Examples 1 to 5

Each organic light emitting diode was manufactured according to the same method as Example 1 except that the host compounds were changed as in Table 1.

Evaluation

Power efficiency of the organic light emitting diodes according to Examples 1 to 5 and Comparative Examples 1 to 5 was evaluated.

Specific measurement methods are as follows, and the results are shown in Table 1.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000 A), while the voltage of the organic light emitting diodes was increased from 0 V to 10 V.

(3) Measurement of Power Efficiency

Power efficiency (cd/A) at the same current density (10 mA/cm$^2$) were calculated by using the luminance, current density, and voltages (V) from the items (1) and (2).

(4) Measurement of Life-span

The results were obtained by measuring a time when current efficiency (cd/A) was decreased down to 90%, while luminance (cd/m$^2$) was maintained to be 6000 cd/m$^2$.

(5) Measurement of Driving Voltage

A driving voltage of each diode was measured using a current-voltage meter (Keithley 2400) at 15 mA/cm$^2$.

TABLE 1

| | Host | Color | Power efficiency (cd/A) | Driving voltage (V) | Life-span T90 (h) |
|---|---|---|---|---|---|
| Example 1 | A-1 | red | 11.1 | 4.54 | 75 |
| Example 2 | A-3 | red | 12.0 | 4.45 | 70 |
| Example 3 | A-17 | red | 13.4 | 4.28 | 95 |
| Example 4 | A-18 | red | 13.8 | 4.15 | 80 |
| Example 5 | A-19 | red | 13.5 | 4.30 | 78 |
| Comparative Example 1 | Y-1 | red | 7.5 | 4.92 | 30 |
| Comparative Example 2 | Y-2 | red | 7.3 | 5.18 | 3 |
| Comparative Example 3 | Y-3 | red | 3.4 | 6.23 | 3 |
| Comparative Example 4 | Y-4 | red | 7.9 | 4.81 | 2 |
| Comparative Example 5 | Y-5 | red | 8.2 | 5.96 | 25 |

Referring to Table 1, the organic light emitting diodes according to Examples 1 to 5 exhibited greatly improved driving voltages, efficiency, and life-span compared with the organic light emitting diodes according to Comparative Examples 1 to 5.

By way of summation and review, an organic light emitting diode converts electrical energy into light. Performance of the organic light emitting diode may be significantly influenced by organic materials disposed between electrodes of the organic light emitting diode.

As described above, embodiments may provide a compound for an organic optoelectronic device that is capable of realizing a high-efficiency and long life-span.

Example embodiments have been disclosed herein, and although specific terms are employed, they are used and are to be interpreted in a generic and descriptive sense only and not for purpose of limitation. In some instances, as would be apparent to one of skill in the art as of the filing of the present application, features, characteristics, and/or elements described in connection with a particular embodiment may be used singly or in combination with features, characteristics, and/or elements described in connection with other embodiments unless otherwise indicated. Accordingly, various changes in form and details may be made without departing from the spirit and scope of the embodiments set forth in the claims.

DESCRIPTION OF SYMBOLS

100, 200: organic light emitting diode

105: organic layer

110: cathode

120: anode

130: light emitting layer

140: hole auxiliary layer

What is claimed is:

1. A compound for an organic optoelectronic device represented by Chemical Formula 1:

[Chemical Formula 1]

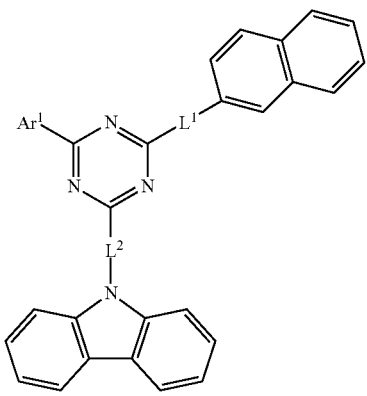

wherein, in Chemical Formula 1,
Ar¹ is a substituted or unsubstituted C6 to C18 aryl group,
L¹ is one of linking groups of Group I:

[Group I]

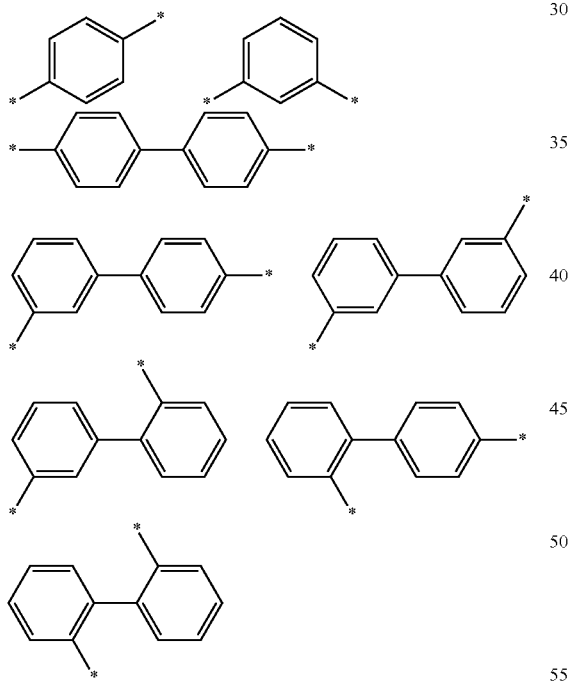

wherein, in Group I, * is a linking point, and
L² is a single bond or a substituted or unsubstituted phenylene group.

2. The compound for an organic optoelectronic device as claimed in claim 1, wherein Ar¹ is a substituted or unsubstituted phenyl group, a substituted or unsubstituted biphenyl group, or a substituted or unsubstituted terphenyl group.

3. The compound for an organic optoelectronic device as claimed in claim 1, wherein Ar¹ is one of substituents of Group II:

[Group II]

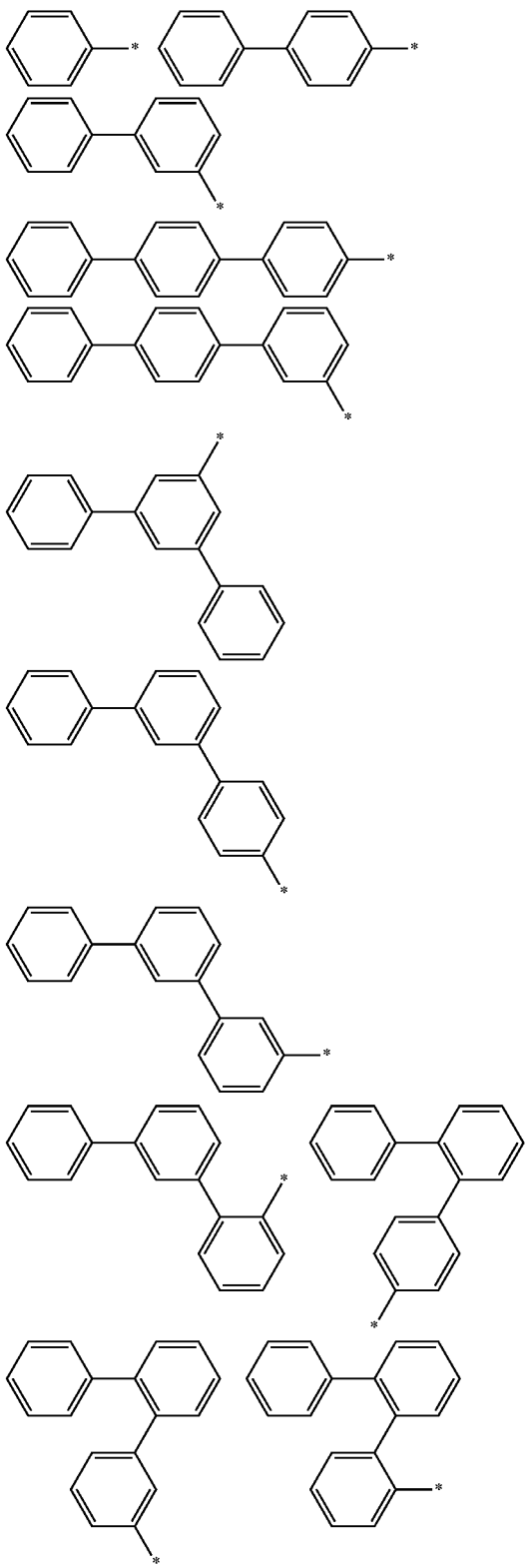

wherein, in Group II, * is a linking point.

4. The compound for an organic optoelectronic device as claimed in claim 1, which is one of compounds of Group A:

[Group A]
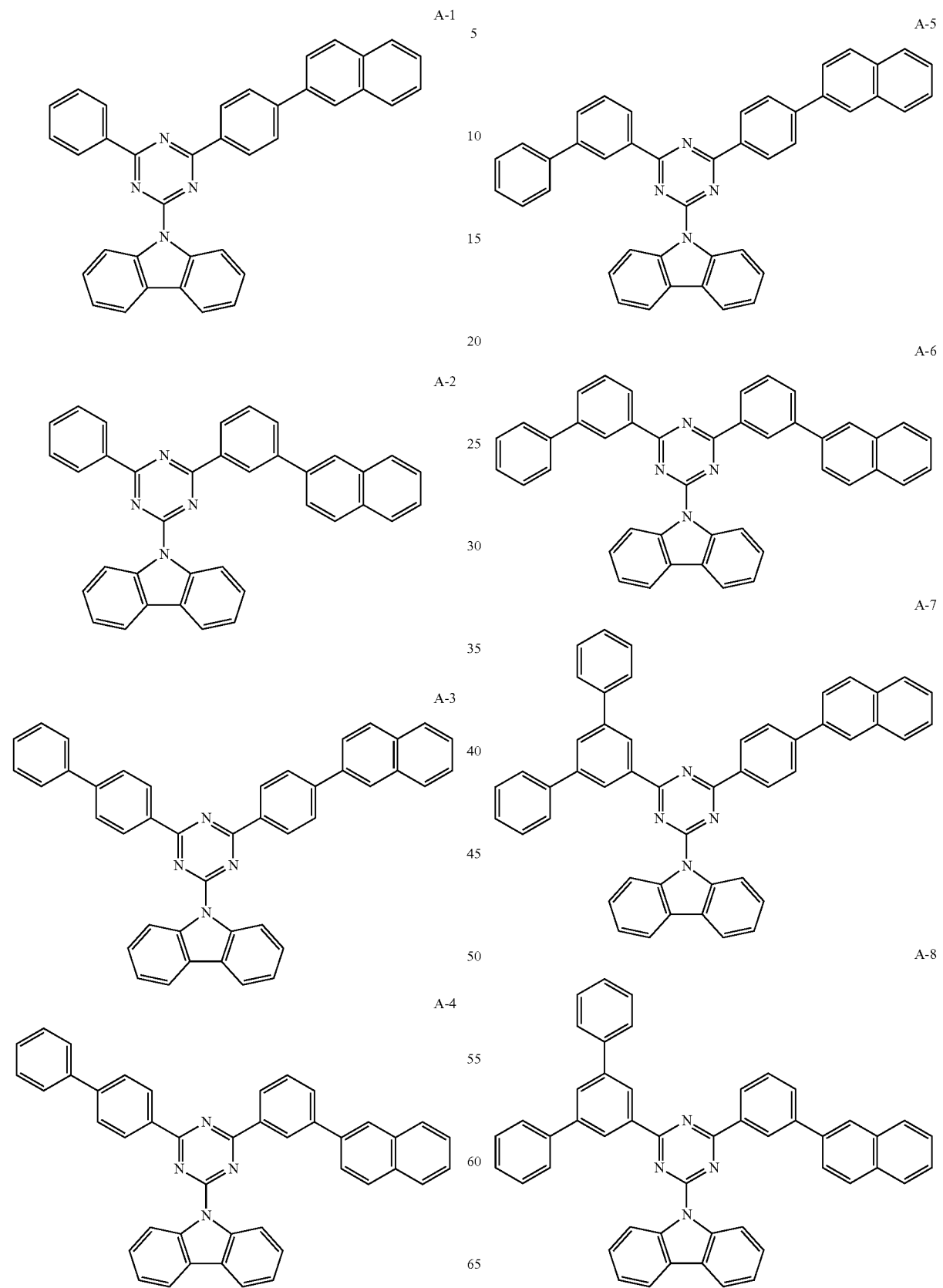

A-9
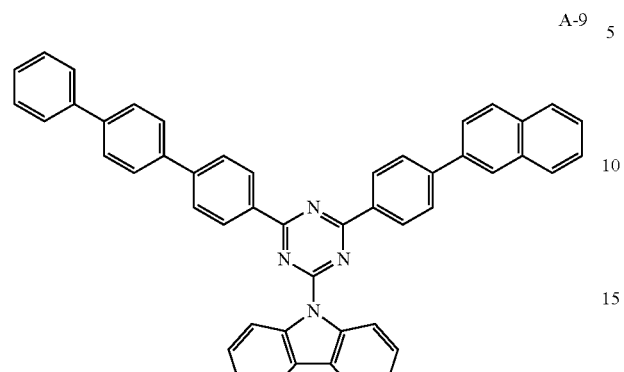
A-10
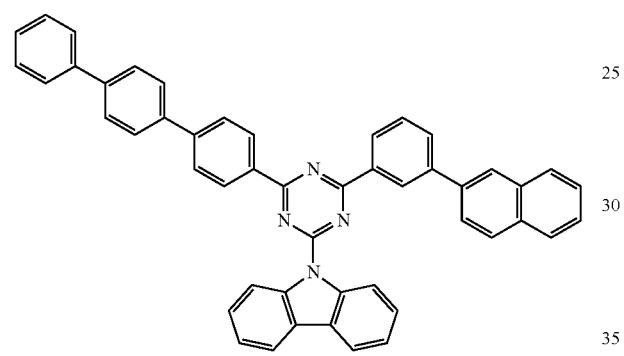
A-11
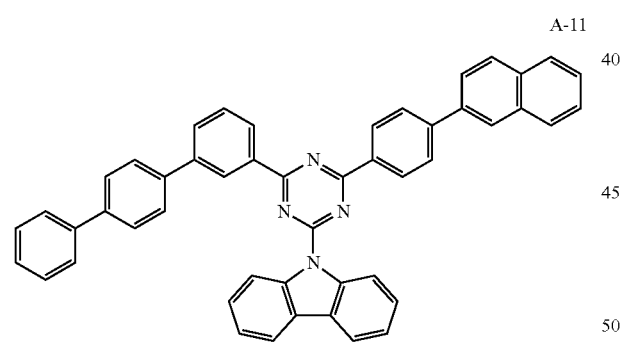
A-12
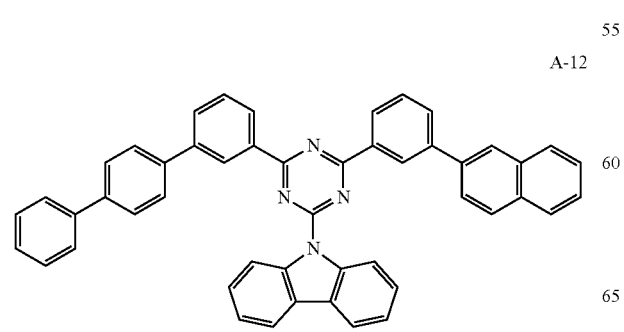
A-13
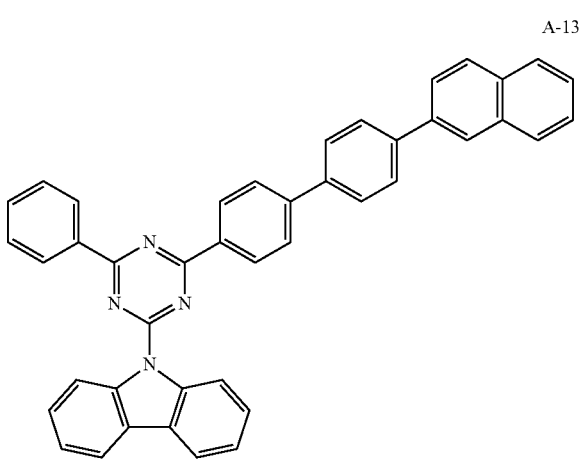
A-14
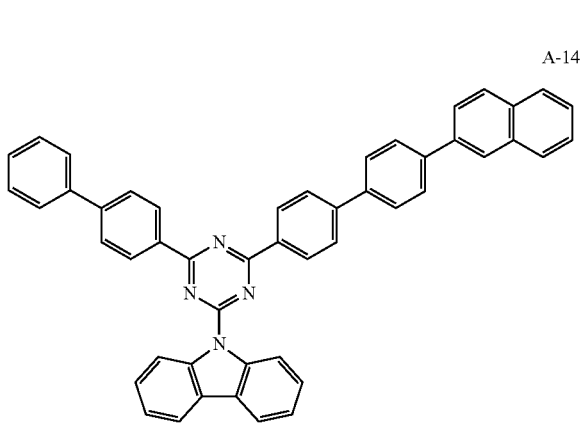
A-15
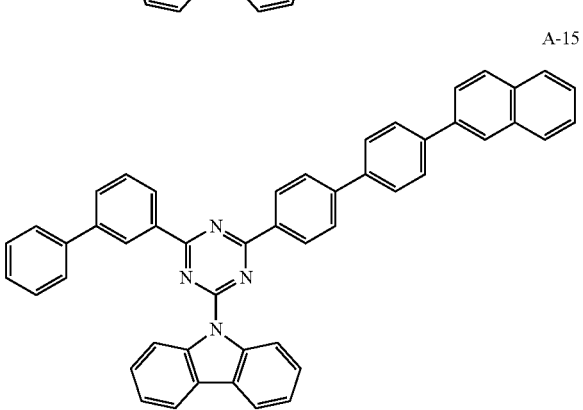
A-16
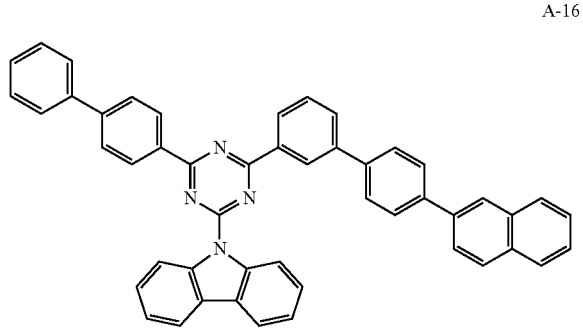

-continued
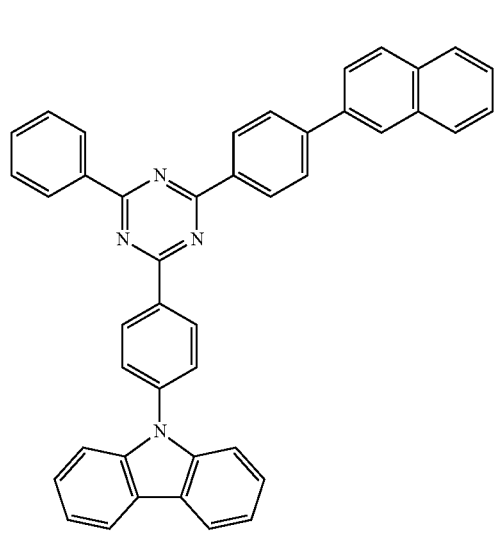
A-17
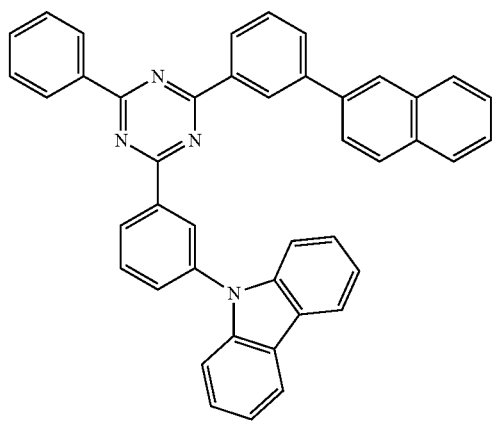
A-20
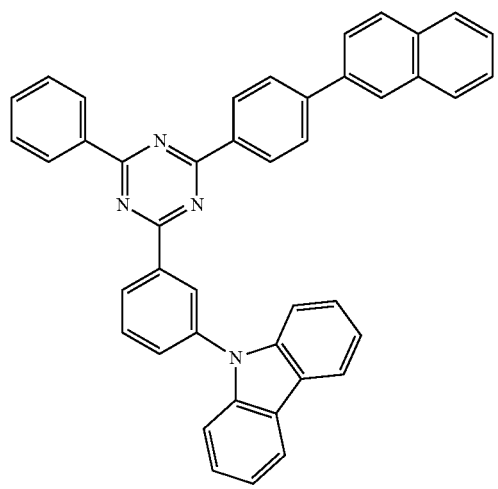
A-18
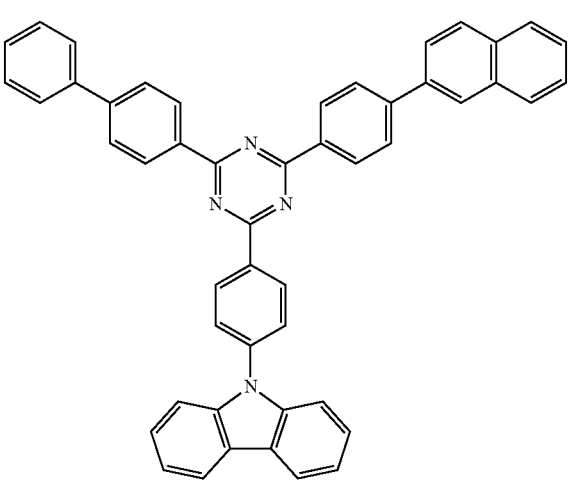
A-21
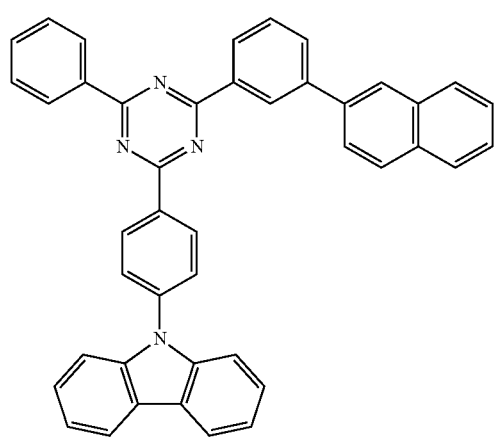
A-19
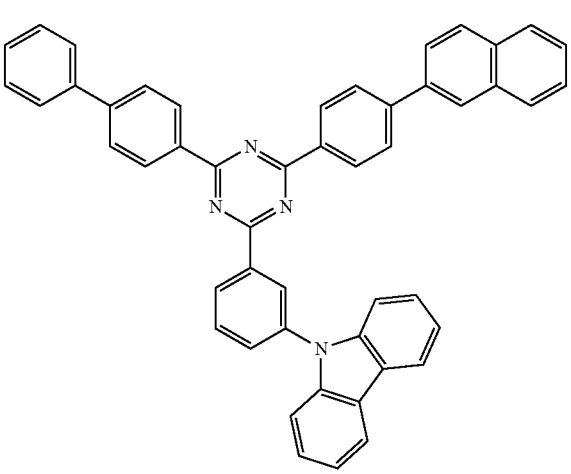
A-22

A-23
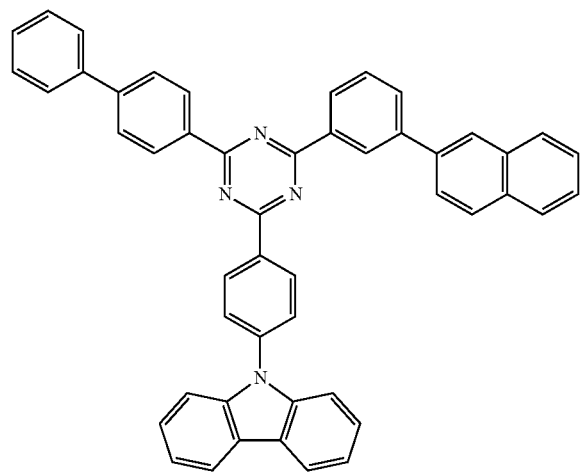
A-24
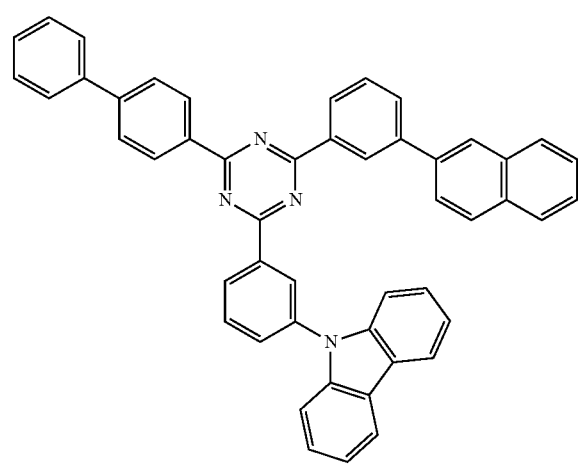
A-25
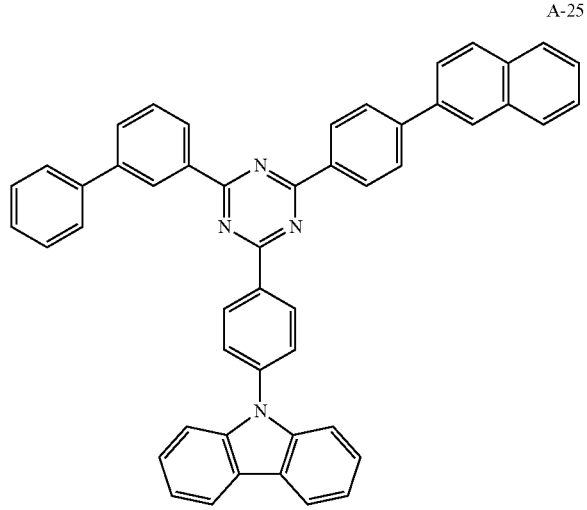
A-26
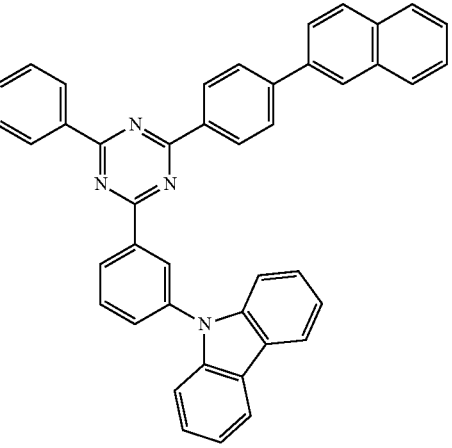
A-27
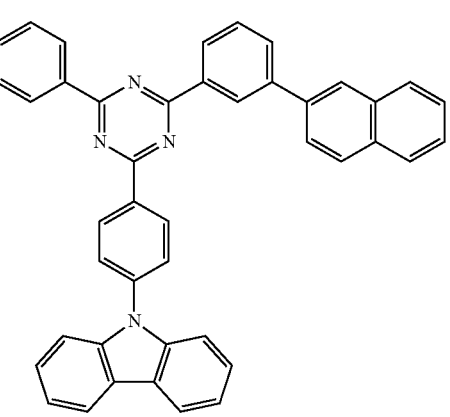
A-28
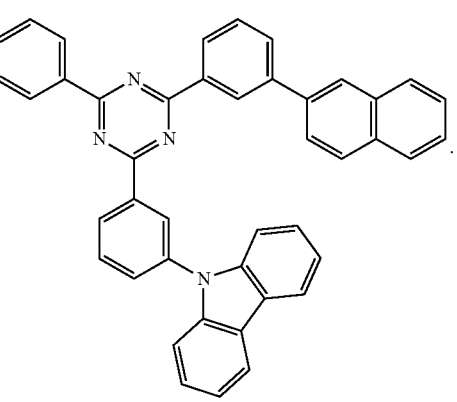
5. An organic optoelectronic device, comprising:
an anode and a cathode facing each other,
at least one organic layer disposed between the anode and the cathode, wherein the at least one organic layer includes the compound for an organic optoelectronic device as claimed in claim 1.

6. The organic optoelectronic device as claimed in claim 5, wherein:

the at least one organic layer includes a light emitting layer, and the light emitting layer comprises the compound.

7. The organic optoelectronic device as claimed in claim 6, wherein the compound is included as a phosphorescent host of the light emitting layer.

8. A display device comprising the organic optoelectronic device as claimed in claim 5.

9. A compound for an organic optoelectronic device, the compound having a structure in which a C6 to C18 aryl group, a naphthyl group, and a carbazolyl group are each bonded to a same 1,3,5-triazine group, wherein:

the aryl group is bonded to the 1,3,5-triazine group via a single bond, the naphthyl group is bonded to the 1,3,5-triazine group via a first linking group that is bonded to the naphthyl group at position 2 or 3 of the naphthyl group, the first linking group being a phenylene or biphenylene group, and the carbazolyl group is bonded to the 1,3,5-triazine group via a second linking group that is bonded to the carbazolyl group at position 9 of the carbazolyl group, the second linking group being a single bond or a phenylene group.

10. An organic optoelectronic device, comprising:

an anode and a cathode facing each other, at least one organic layer disposed between the anode and the cathode, wherein the at least one organic layer includes the compound as claimed in claim 9.

11. A display device comprising the organic optoelectronic device as claimed in claim 10.

12. A compound for an organic optoelectronic device represented by Chemical Formula 1:

[Chemical Formula 1]

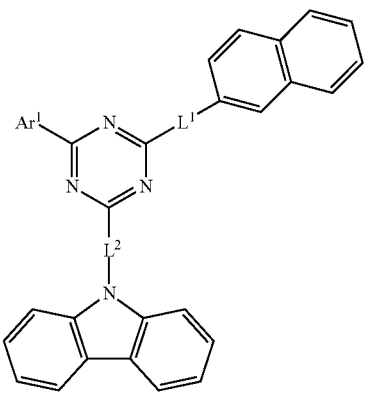

wherein, in Chemical Formula 1, $Ar^1$ is a substituted or unsubstituted C6 to C18 aryl group, $L^1$ is a substituted or unsubstituted C6 to C20 arylene group, and $L^2$ is a single bond or a substituted or unsubstituted phenylene group, wherein:

"substituted" for $Ar^1$ and $L^2$ refers to replacement of at least one hydrogen by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 trifluoroalkyl group, a cyano group, or a combination thereof, and "substituted" for $L^1$ refers to replacement of at least one hydrogen by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C3 to C30 cycloalkyl group, a C3 to C30 heterocycloalkyl group, a C6 to C30 aryl group, a C1 to C20 alkoxy group, a C1 to C10 trifluoroalkyl group, a cyano group, or a combination thereof.

* * * * *